(12) United States Patent
Lilly et al.

(10) Patent No.: US 11,517,477 B2
(45) Date of Patent: Dec. 6, 2022

(54) ADJUSTABLE FLOW GLAUCOMA SHUNTS AND ASSOCIATED SYSTEMS AND METHODS

(71) Applicant: Shifamed Holdings, LLC, Campbell, CA (US)

(72) Inventors: Richard Lilly, San Jose, CA (US); Claudio Argento, Feiton, CA (US); Katherine Sapozhnikov, Campbell, CA (US); Christopher J. Engelman, Los Gatos, CA (US); Jean Orth, Morgan Hill, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 17/765,590

(22) PCT Filed: Oct. 9, 2020

(86) PCT No.: PCT/US2020/055141
§ 371 (c)(1),
(2) Date: Mar. 31, 2022

(87) PCT Pub. No.: WO2021/072315
PCT Pub. Date: Apr. 15, 2021

(65) Prior Publication Data
US 2022/0339035 A1 Oct. 27, 2022

Related U.S. Application Data

(60) Provisional application No. 62/937,667, filed on Nov. 19, 2019, provisional application No. 62/913,703, filed on Oct. 10, 2019.

(51) Int. Cl.
*A61F 9/007* (2006.01)
*B23K 103/14* (2006.01)
*B23K 26/38* (2014.01)

(52) U.S. Cl.
CPC .. *A61F 9/00781* (2013.01); *A61F 2210/0014* (2013.01); *A61F 2240/001* (2013.01);
(Continued)

(58) Field of Classification Search
CPC .......... A61F 9/00781; A61F 2210/0014; A61F 2240/001; A61F 2250/0003; A61F 2250/0013
See application file for complete search history.

(56) References Cited

U.S. PATENT DOCUMENTS

| | | |
|---|---|---|
| 4,401,107 A | 8/1983 | Harber et al. |
| 4,595,390 A | 6/1986 | Hakim et al. |

(Continued)

FOREIGN PATENT DOCUMENTS

| | | |
|---|---|---|
| AU | 2014201621 B2 | 3/2016 |
| AU | 2016201445 B2 | 3/2016 |

(Continued)

OTHER PUBLICATIONS

International Search Report and Written Opinion received for PCT Application No. PCT/US20/55141, filed on Oct. 9, 2020, Applicant: Shifamed Holdings, LLC, dated Jan. 29, 2021, 11 pages.
(Continued)

*Primary Examiner* — Leslie R Deak
(74) *Attorney, Agent, or Firm* — Perkins Coie LLP

(57) ABSTRACT

The present technology is directed to adjustable flow glaucoma shunts and methods for making and using such devices. In many of the embodiments described herein, the shunts include a generally flat frame. The frame can include an elongated portion having a lumen extending therethrough and a bladder portion defining an interior chamber that is in fluid communication with the lumen. When implanted in a patient's eye, aqueous can drain from the anterior chamber to a target outflow location via the lumen and interior (Continued)

chamber. In some embodiments, the shunts include a flow control assembly positioned within the interior chamber of the bladder portion to control the flow of aqueous through the lumen.

42 Claims, 9 Drawing Sheets

(52) U.S. Cl.
CPC .............. *A61F 2250/0003* (2013.01); *A61F 2250/0013* (2013.01); *B23K 26/38* (2013.01); *B23K 2103/14* (2018.08)

(56) References Cited

U.S. PATENT DOCUMENTS

| | | |
|---|---|---|
| 5,070,697 A | 12/1991 | Van Zeggeren |
| 5,123,906 A | 6/1992 | Kelman |
| 6,077,299 A | 6/2000 | Adelberg et al. |
| 6,203,513 B1 | 3/2001 | Yaron et al. |
| 6,261,256 B1 | 7/2001 | Ahmed |
| 6,450,984 B1 | 9/2002 | Lynch et al. |
| 6,508,779 B1 | 1/2003 | Suson |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,736,791 B1 | 5/2004 | Tu et al. |
| 6,789,447 B1 | 9/2004 | Zinck |
| 7,025,740 B2 | 4/2006 | Ahmed |
| 7,207,965 B2 | 4/2007 | Simon |
| 7,354,416 B2 | 4/2008 | Quiroz-Mereado et al. |
| 7,458,953 B2 | 12/2008 | Peyman |
| 7,699,882 B2 | 4/2010 | Stamper et al. |
| 7,717,872 B2 | 5/2010 | Shetty |
| 7,947,008 B2 | 5/2011 | Grahn et al. |
| 8,012,134 B2 | 9/2011 | Claude et al. |
| 8,206,440 B2 | 6/2012 | Guarnieri |
| 8,298,240 B2 | 10/2012 | Giger et al. |
| 8,308,701 B2 | 11/2012 | Horvath et al. |
| 8,506,515 B2 | 8/2013 | Burns et al. |
| 8,540,659 B2 | 9/2013 | Berlin |
| 8,579,848 B2 | 11/2013 | Field et al. |
| 8,585,629 B2 | 11/2013 | Grabner et al. |
| 8,663,303 B2 | 3/2014 | Horvath et al. |
| 8,721,702 B2 | 5/2014 | Romoda et al. |
| 8,753,305 B2 | 6/2014 | Field et al. |
| 8,758,290 B2 | 6/2014 | Horvath et al. |
| 8,765,210 B2 | 7/2014 | Romoda et al. |
| 8,771,220 B2 | 7/2014 | Nissan et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,882,781 B2 | 11/2014 | Smedley et al. |
| 8,915,877 B2 | 12/2014 | Cunningham et al. |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 9,113,994 B2 | 8/2015 | Horvath et al. |
| 9,125,723 B2 | 9/2015 | Horvath et al. |
| 9,192,516 B2 | 11/2015 | Horvath et al. |
| 9,226,851 B2 | 1/2016 | Gunn |
| 9,271,869 B2 | 3/2016 | Horvath et al. |
| 9,283,116 B2 | 3/2016 | Romoda et al. |
| 9,326,891 B2 | 5/2016 | Horvath et al. |
| 9,375,347 B2 | 6/2016 | Stergiopulos |
| 9,393,153 B2 | 7/2016 | Horvath et al. |
| 9,555,410 B2 | 1/2017 | Brammer et al. |
| 9,585,789 B2 | 3/2017 | Silvestrini et al. |
| 9,585,790 B2 | 3/2017 | Horvath et al. |
| 9,592,154 B2 | 3/2017 | Romoda et al. |
| 9,610,195 B2 | 4/2017 | Horvath |
| 9,636,254 B2 | 5/2017 | Yu et al. |
| 9,655,778 B2 | 5/2017 | Tyler |
| 9,655,779 B2 | 5/2017 | Bigler et al. |
| 9,693,900 B2 | 7/2017 | Gallardo Inzunza |
| 9,693,901 B2 | 7/2017 | Horvath et al. |
| 9,757,276 B2 | 9/2017 | Penhasi |
| 9,808,373 B2 | 11/2017 | Horvath et al. |
| 9,877,866 B2 | 1/2018 | Horvath et al. |
| 9,883,969 B2 | 2/2018 | Horvath et al. |
| 9,980,854 B2 | 5/2018 | Horvath et al. |
| 10,004,638 B2 | 6/2018 | Romoda et al. |
| 10,080,682 B2 | 9/2018 | Horvath et al. |
| 10,085,884 B2 | 10/2018 | Reitsamer et al. |
| 10,154,924 B2 | 12/2018 | Clauson et al. |
| 10,159,600 B2 | 12/2018 | Horvath et al. |
| 10,195,078 B2 | 2/2019 | Horvath et al. |
| 10,195,079 B2 | 2/2019 | Horvath et al. |
| 10,231,871 B2 | 3/2019 | Hill |
| 10,238,536 B2 | 3/2019 | Olson et al. |
| 10,285,853 B2 | 5/2019 | Rangel-Friedman et al. |
| 10,307,293 B2 | 6/2019 | Horvath et al. |
| 10,314,743 B2 | 6/2019 | Romoda et al. |
| 10,322,267 B2 | 6/2019 | Hakim |
| 10,369,048 B2 | 8/2019 | Horvath et al. |
| 10,405,903 B1 | 9/2019 | Biesinger et al. |
| 10,335,030 B2 | 10/2019 | Alhourani |
| 10,342,703 B2 | 11/2019 | Siewert et al. |
| 10,463,537 B2 | 11/2019 | Horvath et al. |
| 10,470,927 B2 | 11/2019 | Horvath et al. |
| 10,363,168 B2 | 12/2019 | Schieber et al. |
| 10,492,948 B2 | 12/2019 | Baerveldt |
| 10,524,959 B2 | 1/2020 | Horvath |
| 10,524,958 B2 | 3/2020 | Camras et al. |
| 10,596,035 B2 | 4/2020 | Stergiopulos et al. |
| 10,758,412 B2 | 4/2020 | Velasquez |
| 11,122,975 B2 | 1/2021 | Rodger et al. |
| 10,912,675 B2 | 2/2021 | Lubatschowski |
| 11,166,847 B2 | 2/2021 | Badawi et al. |
| 10,952,897 B1 | 3/2021 | Smith |
| 10,960,074 B2 | 3/2021 | Berdahl |
| 11,039,954 B2 | 6/2021 | Cohen et al. |
| 11,058,581 B2 | 7/2021 | Mixter et al. |
| 11,065,154 B1 | 7/2021 | Sponsel et al. |
| 11,083,624 B2 | 8/2021 | Stein et al. |
| 11,166,848 B2 | 11/2021 | Mixter et al. |
| 11,166,849 B2 | 11/2021 | Mixter et al. |
| 11,291,585 B2 | 4/2022 | Schultz et al. |
| 2001/0011585 A1 | 8/2001 | Cassidy et al. |
| 2002/0177891 A1 | 11/2002 | Miles et al. |
| 2002/0193725 A1 | 12/2002 | Odrich |
| 2003/0127090 A1 | 7/2003 | Gifford et al. |
| 2003/0163079 A1 | 8/2003 | Burnett |
| 2004/0010219 A1 | 1/2004 | McCusker et al. |
| 2004/0254520 A1 | 12/2004 | Porteous et al. |
| 2005/0049578 A1 | 3/2005 | Tu et al. |
| 2006/0155300 A1 | 7/2006 | Stamper et al. |
| 2007/0010837 A1 | 1/2007 | Tanaka |
| 2007/0078371 A1 | 4/2007 | Brown et al. |
| 2007/0088432 A1 | 4/2007 | Solovay et al. |
| 2008/0077071 A1 | 3/2008 | Yaron et al. |
| 2008/0119891 A1 | 5/2008 | Miles et al. |
| 2008/0125691 A1 | 5/2008 | Yaron et al. |
| 2009/0036818 A1 | 2/2009 | Grahn et al. |
| 2009/0243956 A1 | 10/2009 | Keilman et al. |
| 2009/0326517 A1 | 12/2009 | Bork et al. |
| 2010/0234791 A1 | 9/2010 | Lynch et al. |
| 2010/0241077 A1 | 9/2010 | Geipel et al. |
| 2011/0105986 A1 | 5/2011 | Bronstein et al. |
| 2012/0065570 A1 | 3/2012 | Yeung et al. |
| 2012/0089073 A1 | 4/2012 | Cunningham, Jr. |
| 2013/0131577 A1 | 5/2013 | Bronstein et al. |
| 2013/0150773 A1 | 6/2013 | Nissan et al. |
| 2013/0150776 A1 | 6/2013 | Bohm et al. |
| 2013/0158381 A1 | 6/2013 | Rickard |
| 2013/0197621 A1 | 8/2013 | Ryan et al. |
| 2013/0199646 A1 | 8/2013 | Brammer et al. |
| 2013/0205923 A1 | 8/2013 | Brammer et al. |
| 2013/0211312 A1 | 8/2013 | Gelvin |
| 2013/0267887 A1 | 10/2013 | Kahook et al. |

(56) References Cited

U.S. PATENT DOCUMENTS

| | | |
|---|---|---|
| 2013/0317412 A1 | 11/2013 | Dacquay et al. |
| 2013/0338564 A1 | 12/2013 | Rickard et al. |
| 2014/0046439 A1 | 2/2014 | Dos Santos et al. |
| 2014/0081195 A1 | 3/2014 | Clauson et al. |
| 2014/0309611 A1 | 10/2014 | Wilt et al. |
| 2015/0011926 A1 | 1/2015 | Reitsamer et al. |
| 2015/0034217 A1 | 2/2015 | Vad |
| 2015/0045716 A1 | 2/2015 | Gallardo Inzunza |
| 2015/0142049 A1 | 5/2015 | Delgado et al. |
| 2015/0230843 A1 | 8/2015 | Palmer et al. |
| 2015/0313603 A1 | 11/2015 | Bodewadt et al. |
| 2016/0151179 A1 | 6/2016 | Favier et al. |
| 2016/0220794 A1 | 8/2016 | Negre |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0287439 A1 | 10/2016 | Stergiopulos |
| 2016/0354244 A1 | 12/2016 | Horvath et al. |
| 2016/0354245 A1 | 12/2016 | Horvath et al. |
| 2017/0027582 A1 | 2/2017 | Khoury et al. |
| 2017/0071791 A1 | 3/2017 | Piven |
| 2017/0087016 A1 | 3/2017 | Camras |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0312125 A1 | 11/2017 | Clauson et al. |
| 2017/0348149 A1 | 12/2017 | Stergiopulos et al. |
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0092775 A1 | 4/2018 | de Juan, Jr. et al. |
| 2018/0147089 A1 | 5/2018 | Horvath et al. |
| 2018/0206878 A1 | 7/2018 | Uspenski et al. |
| 2018/0250166 A1 | 9/2018 | Lubatschowski |
| 2019/0000673 A1 | 1/2019 | Fjield et al. |
| 2019/0021907 A1 | 1/2019 | Horvath et al. |
| 2019/0038462 A1 | 2/2019 | Vandiest et al. |
| 2019/0046356 A1 | 2/2019 | Laroche |
| 2019/0060118 A1 | 2/2019 | Hill |
| 2019/0133826 A1 | 3/2019 | Horvath et al. |
| 2019/0121278 A1 | 4/2019 | Kawamura et al. |
| 2019/0142632 A1 | 5/2019 | Badawi et al. |
| 2019/0167475 A1 | 6/2019 | Horvath et al. |
| 2019/0240069 A1 | 8/2019 | Horvath et al. |
| 2019/0247231 A1 | 8/2019 | McClunan |
| 2019/0274881 A1 | 9/2019 | Romoda et al. |
| 2019/0274882 A1 | 9/2019 | Romoda et al. |
| 2019/0307608 A1 | 10/2019 | Lee et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2019/0358086 A1 | 11/2019 | Camras et al. |
| 2019/0374384 A1 | 12/2019 | Xie et al. |
| 2020/0069469 A1 | 3/2020 | Horvath et al. |
| 2020/0085620 A1 | 3/2020 | Euteneuer et al. |
| 2020/0121503 A1 | 4/2020 | Badawi et al. |
| 2020/0121504 A1 | 4/2020 | Stegmann et al. |
| 2020/0170839 A1 | 6/2020 | Borrmann et al. |
| 2020/0179171 A1 | 6/2020 | Grimaldi et al. |
| 2020/0214891 A1 | 7/2020 | Bigler et al. |
| 2020/0229977 A1 | 7/2020 | Mixter et al. |
| 2020/0229980 A1 | 7/2020 | Horvath |
| 2020/0229981 A1 | 7/2020 | Mixter et al. |
| 2020/0229982 A1 | 7/2020 | Mixter et al. |
| 2020/0246188 A1 | 8/2020 | Horvath et al. |
| 2020/0261271 A1 | 8/2020 | Horvath et al. |
| 2020/0276050 A1 | 9/2020 | Simons et al. |
| 2020/0306086 A1 | 10/2020 | Da Silva Curiel et al. |
| 2020/0345549 A1 | 11/2020 | Lu et al. |
| 2021/0015665 A1 | 1/2021 | Hacker et al. |
| 2021/0030590 A1 | 2/2021 | Blanda et al. |
| 2021/0038158 A1 | 2/2021 | Haffner et al. |
| 2021/0069486 A1 | 3/2021 | Hakim |
| 2021/0106462 A1 | 4/2021 | Sherwood et al. |
| 2021/0137736 A1 | 5/2021 | Cavuto et al. |
| 2021/0161713 A1 | 6/2021 | Bouremel et al. |
| 2021/0196516 A1 | 7/2021 | Ianchulev |
| 2021/0205132 A1 | 7/2021 | Horvath et al. |
| 2021/0212858 A1 | 7/2021 | Tran et al. |
| 2021/0251806 A1* | 8/2021 | Schultz ............... A61F 9/00781 |
| 2021/0298948 A1 | 9/2021 | Haffner et al. |
| 2021/0315806 A1 | 10/2021 | Haffner |
| 2021/0330499 A1 | 10/2021 | Wardle et al. |
| 2022/0142818 A1* | 5/2022 | Chang ............... A61F 9/00781 |
| 2022/0202613 A1* | 6/2022 | Chang ............... A61F 9/00781 |

FOREIGN PATENT DOCUMENTS

| | | |
|---|---|---|
| AU | 2018200325 A1 | 2/2018 |
| AU | 2017274654 | 12/2018 |
| AU | 2020201818 | 4/2020 |
| AU | 2017439185 | 5/2020 |
| AU | 2018412569 | 10/2020 |
| BR | 112017025859 A2 | 8/2018 |
| BR | 112020008969 | 10/2020 |
| CA | 2987953 A1 | 12/2016 |
| CA | 3080713 | 5/2019 |
| CA | 3093160 | 9/2019 |
| CN | 108743016 A | 11/2018 |
| CN | 111405875 | 7/2020 |
| CO | 2020011460 | 11/2020 |
| DE | 10217061 | 3/2003 |
| DE | 102010015447 A1 | 10/2011 |
| DE | 102017124885 A1 | 4/2019 |
| DE | 102018112065 A1 | 11/2019 |
| DE | 102019204846 A1 | 10/2020 |
| EP | 1292256 A1 | 3/2003 |
| EP | 1737531 A2 | 1/2007 |
| EP | 3302381 A1 | 4/2018 |
| EP | 1765234 | 10/2019 |
| EP | 2999430 | 11/2019 |
| EP | 2677981 | 4/2020 |
| EP | 3659495 | 6/2020 |
| EP | 3518846 | 8/2020 |
| EP | 3666236 | 8/2020 |
| EP | 3687374 | 8/2020 |
| EP | 3706653 | 9/2020 |
| EP | 3730104 | 10/2020 |
| EP | 3735947 | 11/2020 |
| EP | 3773377 | 2/2021 |
| EP | 3846747 | 7/2021 |
| EP | 3846748 | 7/2021 |
| EP | 3329884 | 8/2021 |
| EP | 2389138 | 9/2021 |
| EP | 3870120 | 9/2021 |
| EP | 3313335 | 11/2021 |
| ES | 2725550 | 9/2019 |
| HK | 1252748 | 5/2019 |
| HU | E043303 | 8/2019 |
| JP | 5576427 B2 | 8/2014 |
| JP | 2018519892 | 7/2018 |
| JP | 2018130580 | 8/2018 |
| JP | 2019517366 | 6/2019 |
| JP | 2019205934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO2004081613 | 9/2004 |
| WO | WO2007011302 A1 | 1/2007 |
| WO | WO2010111528 | 9/2010 |
| WO | WO2014130574 | 8/2014 |
| WO | WO2016149425 | 9/2016 |
| WO | WO2016196841 A1 | 12/2016 |
| WO | WO2018229766 | 12/2018 |
| WO | WO2019094004 A1 | 5/2019 |

(56) References Cited

FOREIGN PATENT DOCUMENTS

| | | |
|---|---|---|
| WO | WO2019165053 | 8/2019 |
| WO | WO2019172940 | 9/2019 |
| WO | WO2020150663 | 7/2020 |
| WO | WO2020215068 | 10/2020 |
| WO | WO2020223491 | 11/2020 |
| WO | WO2020231993 | 11/2020 |
| WO | WO2020247365 | 12/2020 |
| WO | WO2020261184 | 12/2020 |
| WO | WO2021007294 | 1/2021 |
| WO | WO2021007296 | 1/2021 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |
| WO | WO2021188952 | 9/2021 |
| WO | WO2021204312 | 10/2021 |
| WO | WO 2021212007 | 10/2021 |
| WO | WO2021230887 | 11/2021 |
| ZA | 201708295 | 5/2020 |

OTHER PUBLICATIONS

International Search Report and Written Opinion received for PCT Application No. PCT/US18/43158, filed on Jul. 20, 2018, Applicant: Shifamed Holdings, LLC, dated Nov. 23, 2018, 12 pages.

International Search Report and Written Opinion received for PCT Application No. PCT/US20/41159, filed on Jul. 8, 2020, Applicant: Shifamed Holdings, LLC, dated Oct. 28, 2020, 13 pages.

International Search Report and Written Opinion received for PCT Application No. PCT/US20/41152, filed on Jul. 8, 2020, Applicant: Shifamed Holdings, LLC, dated Oct. 28, 2020, 13 pages.

International Search Report and Written Opinion received for PCT Application No. PCT/US20/14186, filed on Jan. 17, 2020, Applicant: Shifamed Holdings, LLC, dated Jun. 4, 2020, 13 pages.

International Search Report and Written Opinion received for PCT Application No. PCT/US21/14774, filed on Jan. 22, 2021, Applicant: Shifamed Holdings, LLC, dated May 12, 2021, 10 pages.

International Search Report and Written Opinion received for PCT Application No. PCT/US21/17962, filed on Feb. 12, 2021, Applicant: Shifamed Holdings, LLC, dated Jun. 7, 2021, 12 pages.

International Search Report and Written Opinion received for PCT Application No. PCT/US21/23238, filed on Mar. 19, 2021, Applicant: Shifamed Holdings, LLC, dated Jul. 8, 2021, 10 pages.

International Search Report and Written Opinion received for PCT Application No. PCT/US21/18601, filed on Feb. 18, 2021, Applicant: Shifamed Holdings, LLC, dated Jul. 19, 2021, 12 pages.

International Search Report and Written Opinion received for PCT Application No. PCT/US21/27742, filed on Apr. 16, 2021, Applicant: Shifamed Holdings, LLC, dated Oct. 7, 2021, 13 pages.

International Search Report and Written Opinion received for PCT Application No. PCT/US21/47013, filed on Aug. 20, 2021, Applicant: Shifamed Holdings, LLC, dated Nov. 26, 2021, 28 pages.

International Search Report and Written Opinion received for PCT Application No. PCT/US21/49140, filed on Sep. 3, 2021, Applicant: Shifamed Holdings, LLC, dated Dec. 7, 2021, 22 pages.

International Search Report and Written Opinion received for PCT Application No. PCT/US21/55258, filed on Oct. 15, 2021, Applicant: Shifamed Holdings, LLC, dated Feb. 28, 2022, 18 pages.

International Search Report and Written Opinion received for PCT Application No. PCT/US22/13336, filed on Jan. 21, 2022, Applicant: Shifamed Holdings, LLC, dated Apr. 11, 2022, 9 pages.

International Search Report and Written Opinion received for PCT Application No. PCT/US20/55144, filed on Oct. 9, 2020, Applicant: Shifamed Holdings, LLC, dated Feb. 1, 2021, 16 pages.

* cited by examiner

ADJUSTABLE FLOW GLAUCOMA SHUNTS AND ASSOCIATED SYSTEMS AND METHODS

CROSS-REFERENCE TO RELATED APPLICATION(S)

This application is a 35 U.S.C. § 371 U.S. National Phase application of International Patent Application No. PCT/US2020/055141, filed Oct. 9, 2020, and titled ADJUSTABLE FLOW GLAUCOMA SHUNTS AND ASSOCIATED SYSTEMS AND METHODS, which claims priority to the following provisional patent applications:

U.S. Provisional Patent Application No. 62/913,703, filed Oct. 10, 2019; and

U.S. Provisional Patent Application No. 62/937,667, filed Nov. 19, 2019.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology relates to adjustable flow glaucoma shunts and methods for making and using such devices.

BACKGROUND

Glaucoma is a degenerative ocular condition involving damage to the optic nerve that can cause progressive and irreversible vision loss. Glaucoma is frequently associated with ocular hypertension, an increase in pressure within the eye, and may result from an increase in production of aqueous humor ("aqueous") within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the venous vessels of the eye. Glaucoma is typically caused by a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1A:
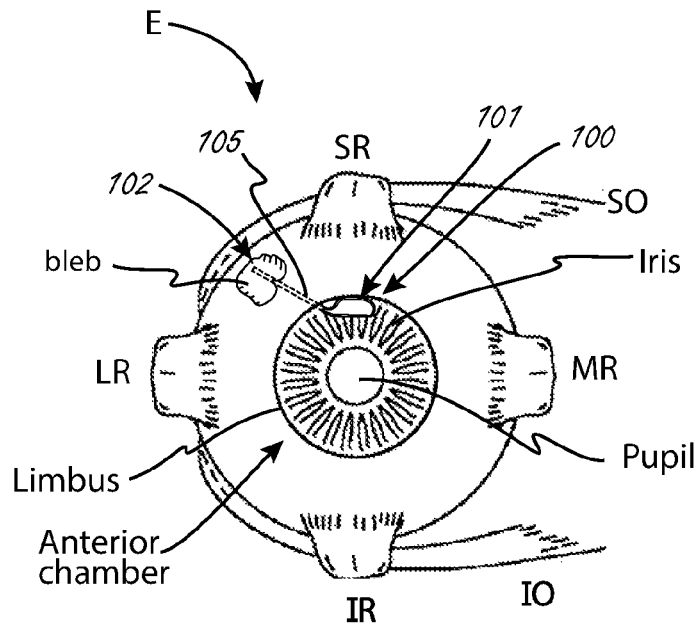
FIG. 1A is a simplified front view of an eye E with an implanted shunt.

The present technology is directed to adjustable flow glaucoma shunts and methods for making and using such devices. In many of the embodiments described herein, the shunts include a generally flat outer frame. The frame can include an elongated portion having a lumen extending therethrough and a bladder portion defining an interior chamber that is in fluid communication with the lumen. When implanted in a patient's eye, aqueous can drain from the anterior chamber to a target outflow location by flowing through the lumen and the interior chamber. In some embodiments, the shunts include a flow control assembly positioned within the interior chamber of the bladder portion to control the flow of aqueous through the lumen.

As provided above, in some embodiments the present technology includes flow control assemblies for controlling the flow of fluid through a shunt. The flow control assemblies generally include an anchoring element, one or more actuation elements, and a gating element. The anchoring element can be designed to reside within a portion of the shunt (e.g., within a chamber formed by the frame). The gating element can include a lever or arm that can at least partially block a portion of the shunt lumen. The actuation element can move the gating element back and forth to selectively block and/or unblock the lumen, thereby decreasing or increasing flow through the shunt.

The present technology further includes methods of manufacturing the shunts and flow control assemblies described herein. The methods can include fabricating (e.g., laser cutting) a unitary structure corresponding to a flow control assembly from a single pierce of material (e.g., a sheet or a strip of nitinol). The unitary structure can include an anchoring element, an actuation element, and a gating element. The actuation element can have a first end portion extending from the gating element and a second end portion not connected to another portion of the unitary structure. To form the flow control assembly from the unitary structure, the actuation element can be deformed relative to its preferred geometry (e.g., prestressed and/or prestrained) and the second end portion of the actuation element can be secured to the anchoring. With the flow control assembly formed, it can be coupled to the shun such that the flow control assembly is configured to at least partially control the flow of fluid through the shunt.

Specific details of various embodiments of the present technology are described below with reference to FIGS. 1A-5D. Although many of the embodiments are described below with respect to adjustable flow glaucoma shunts and associated methods, other embodiments are within the scope of the present technology. Additionally, other embodiments of the present technology can have different configurations, components, and/or procedures than those described herein. For instance, shunts configured in accordance with the present technology may include additional elements and features beyond those described herein, or other embodiments may not include several of the elements and features shown and described herein. Moreover, the use of the term "shunt" herein generally refers to the overall devices described herein, but in some aspects the term "shunt" and "tube" are used interchangeably.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

Although certain embodiments herein are described in terms of shunting fluid from an anterior chamber of an eye, one of skill in the art will appreciate that the present technology can be readily adapted to shunt fluid from and/or between other portions of the eye, or, more generally, from and/or between a first body region and a second body region. Moreover, while the certain embodiments herein are described in the context of glaucoma treatment, any of the embodiments herein, including those referred to as "glaucoma shunts" or "glaucoma devices" may nevertheless be used and/or modified to treat other diseases or conditions, including other diseases or conditions of the eye or other body regions. For example, the systems described herein can be used to treat diseases characterized by increased pressure and/or fluid build-up, including but not limited to heart failure (e.g., heart failure with preserved ejection fraction, heart failure with reduced ejection fraction, etc.), pulmonary failure, renal failure, hydrocephalus, and the like. Moreover, while generally described in terms of shunting aqueous, the systems described herein may be applied equally to shunting other fluid, such as blood or cerebrospinal fluid, between the first body region and the second body region.

The headings provided herein are for convenience only and do not interpret the scope or meaning of the claimed present technology.

A. Implantable Shunts for Glaucoma Treatment

Glaucoma refers to a group of eye diseases associated with damage to the optic nerve which eventually result in vision loss and blindness. As noted above, glaucoma is a degenerative ocular condition characterized by an increase in pressure within the eye resulting from an increase in production of aqueous within the eye and/or a decrease in the rate of outflow of aqueous from within the eye into the blood stream. The increased pressure leads to injury of the optic nerve over time. Unfortunately, patients often do not present with symptoms of increased intraocular pressure until the onset of glaucoma. As such, patients typically must be closely monitored once increased pressure is identified even if they are not symptomatic. The monitoring continues over the course of the disease so clinicians can intervene early to stem progression of the disease. Monitoring pressure requires patients to visit a clinic site on a regular basis which is expensive, time-consuming, and inconvenient. The early stages of glaucoma are typically treated with drugs (e.g., eye drops) and/or laser therapy. When drug/laser treatments no longer suffice, however, surgical approaches can be used. Surgical or minimally invasive approaches primarily attempt to increase the outflow of aqueous from the anterior chamber to the blood stream either by the creation of alternative fluid paths or the augmentation of the natural paths for aqueous outflow.

Figure 1B:
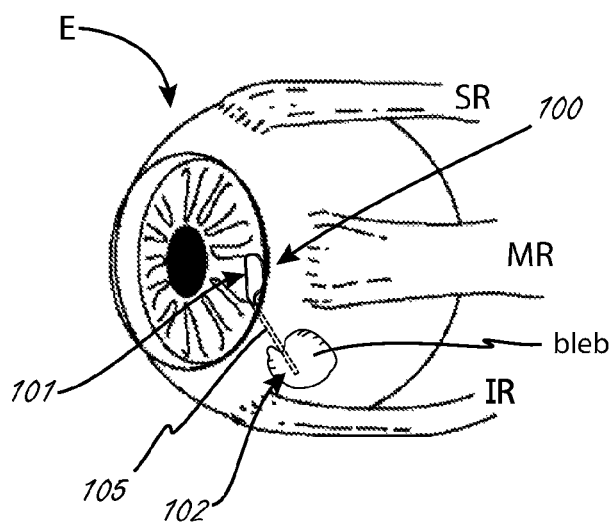
FIG. 1B is an isometric view of the eye capsule of FIG. 1A.

FIGS. 1A and 1B illustrate a human eye E and suitable location(s) in which a shunt may be implanted within the eye E in accordance with embodiments of the present technology. More specifically, FIG. 1A is a simplified front view of the eye E with an implanted shunt 100, and FIG. 1B is an isometric view of the eye E and the shunt 100 of FIG. 1A. Referring first to FIG. 1A, the eye E includes a number of muscles to control its movement, including a superior rectus SR, inferior rectus IR, lateral rectus LR, medial rectus MR, superior oblique SO, and inferior oblique IO. The eye E also includes an iris, pupil, and limbus.

Referring to FIGS. 1A and 1B together, the shunt 100 can have a drainage element 105 (e.g., a drainage tube) positioned such that an inflow portion 101 is positioned in an anterior chamber of the eye E, and an outflow portion 102 is positioned at a different location within the eye E, such as a bleb space. The shunt 100 can be implanted in a variety of orientations. For example, when implanted, the drainage element 105 may extend in a superior, inferior, medial, and/or lateral direction from the anterior chamber. Depending upon the design of the shunt 100, the outflow portion 102 can be placed in a number of different suitable outflow locations (e.g., between the choroid and the sclera, between the conjunctiva and the sclera, etc.).

Outflow resistance can change over time for a variety of reasons, e.g., as the outflow location goes through its healing process after surgical implantation of a shunt (e.g., shunt 100) or further blockage in the drainage network from the anterior chamber through the trabecular meshwork, Schlemm's canal, the collector channels, and eventually into the vein and the body's circulatory system. Accordingly, a clinician may desire to modify the shunt after implantation to either increase or decrease the outflow resistance in response to such changes or for other clinical reasons. For example, in many procedures the shunt is modified at implantation to temporarily increase its outflow resistance. After a period of time deemed sufficient to allow for healing of the tissues and stabilization of the outflow resistance, the modification to the shunt is reversed, thereby decreasing the outflow resistance. In another example, the clinician may implant the shunt and after subsequent monitoring of intraocular pressure determine a modification of the drainage rate through the shunt is desired. Such modifications can be invasive, time-consuming, and/or expensive for patients. If such a procedure is not followed, however, there is a high likelihood of creating hypotony (excessively low eye pressure), which can result in further complications, including damage to the optic nerve. In contrast, intraocular shunting systems configured in accordance with embodiments of the present technology allow the clinician to selectively adjust the flow of fluid through the shunt after implantation without additional invasive surgical procedures.

The shunts described herein can be implanted having a first drainage rate and subsequently remotely adjusted to achieve a second drainage rate. The adjustment can be based on the needs of the individual patient. For example, the shunt may be implanted at a first lower flow rate and subsequently adjusted to a second higher flow rate as clinically necessary. The shunts described herein can be delivered using either ab interno or ab externo implant techniques, and can be delivered via needles. The needles can have a variety of shapes and configurations to accommodate the various shapes of the shunts described herein. For example, in some embodiments, the needles may be hinged to facilitate implantation through the sclera. Details of the implant procedure, the implant devices, and bleb formation are described in greater detail in International Patent Application No. PCT/US20/

41152, titled "MINIMALLY INVASIVE BLEB FORMATION DEVICES AND METHODS FOR USING SUCH DEVICES," filed Jul. 8, 2020, the disclosure of which is hereby incorporated by reference herein for all purposes.

In many of the embodiments described herein, the flow control assemblies are configured to introduce features that selectively impede or attenuate fluid flow through the shunt during operation. In this way, the flow control assemblies can incrementally or continuously change the flow resistance through the shunt to selectively regulate pressure and/or flow. The flow control assemblies configured in accordance with the present technology can accordingly adjust the level of interference or compression between a number of different positions, and accommodate a multitude of variables (e.g., IOP, aqueous production rate, native aqueous outflow resistance, and/or native aqueous outflow rate) to precisely regulate flow rate through the shunt.

The disclosed flow control assemblies can be operated using energy. This feature allows such devices to be implanted in the patient and then modified/adjusted over time without further invasive surgeries or procedures for the patient. Further, because the devices disclosed herein may be actuated via energy, such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

B. Selected Embodiments of Adjustable Flow Glaucoma Shunts

Figure 2A:
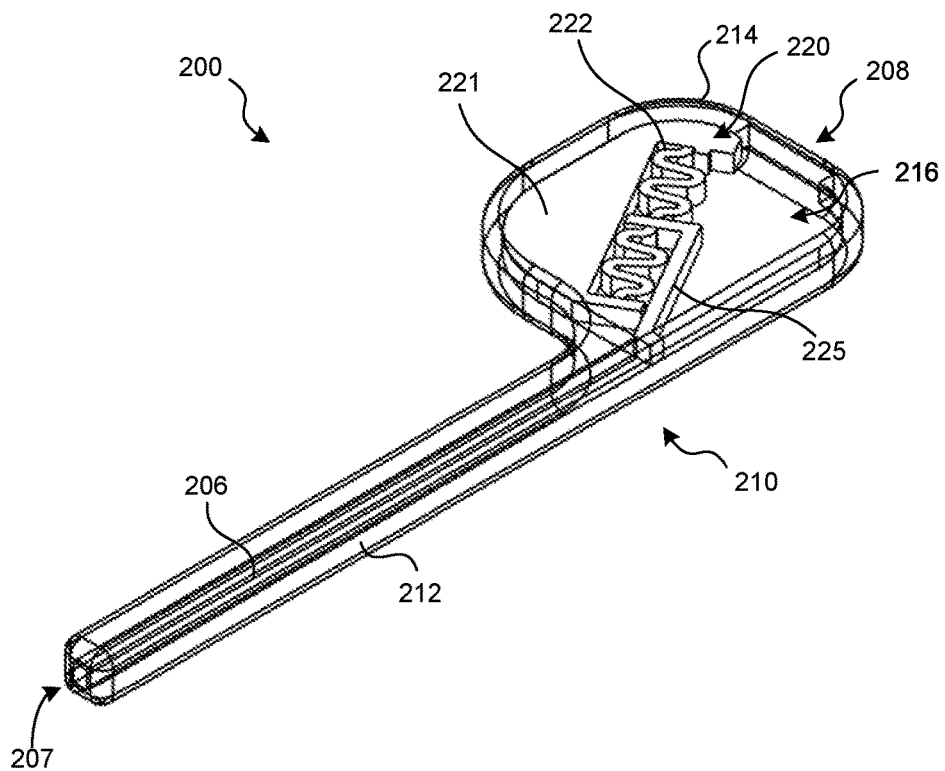
FIGS. 2A-2E illustrate an adjustable flow glaucoma shunt configured in accordance with select embodiments of the present technology.
Figure 2B:
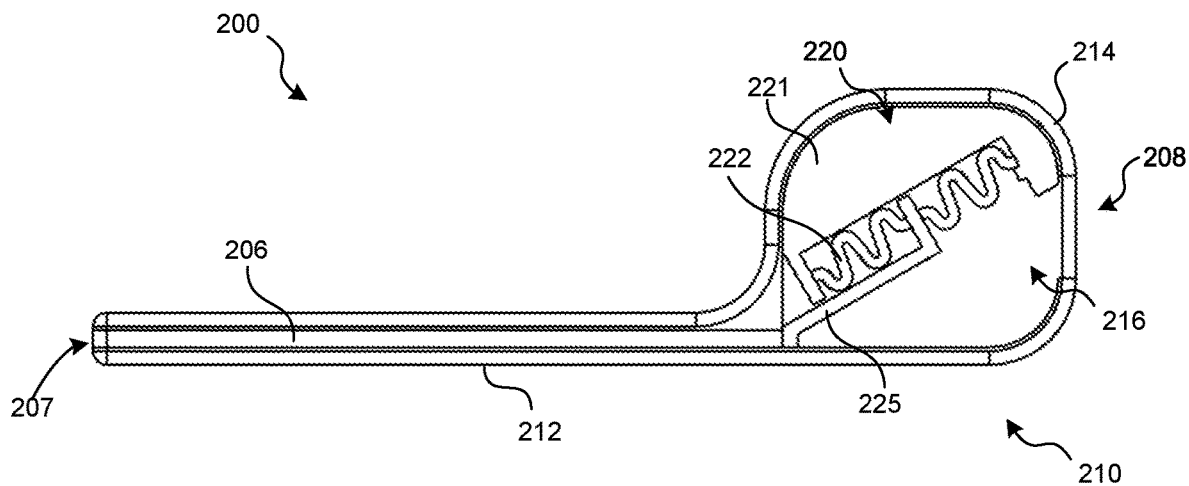

As provided above, the present technology is directed to adjustable flow glaucoma shunts. FIGS. 2A-2E illustrate an adjustable flow shunt 200 ("shunt 200") configured in accordance with select embodiments of the present technology. Referring first to FIGS. 2A and 2B, which are isometric and top views, respectively, of the shunt 200, the shunt 200 includes a frame 210 (which can also be referred to as a "body element," "drainage element," or "shunting element") having an elongated portion 212 and a bladder portion 214. The bladder portion 214 can define an interior chamber 216 for housing various components of the shunt 200, described below. A lumen 206 can extend through the elongated portion 212 and be fluidly coupled to the interior chamber 216 of the bladder portion 214. The lumen 206 can have a circular, oval, rectangular, or other cross-sectional shape. In some embodiments, for example, the lumen 206 has a rectangular cross-section to minimize a dimension (e.g., a height, width, diameter, etc.) of the elongated portion 212. The elongated portion 212 can have a cross-sectional shape matching the lumen 206 (e.g., rectangular). In some embodiments, the elongated portion 212 defines the lumen 206. In other embodiments, a flow tube (not shown) is positioned within the elongated portion 212 to form the lumen 206. Although the frame 210 is illustrated as transparent in FIGS. 2A and 2B so that internal components of the shunt 200 can be depicted, the frame 210 need not be transparent and can substantially encase portions of the shunt, as described in greater detail with respect to FIGS. 2D and 2E.

In some embodiments, at least a portion of the elongated portion 212 is configured for placement within an anterior chamber of an eye in a region outside of the optical field of view of the eye, and the bladder portion 214 is configured for placement within a desired outflow location, such as a subconjunctival bleb space. In such embodiments, aqueous can flow from the anterior chamber and into the lumen 206 via a first (e.g., inflow) port 207. The aqueous can then flow through the lumen 206 and into the interior chamber 216. Once in the interior chamber 216, the aqueous may drain into the desired outflow location via a second (e.g., outflow) port 208. In other embodiments, the orientation of the shunt 200 can be reversed when implanted, such that the bladder portion 214 is positioned in the anterior chamber and the first port 207 of the elongated portion 212 is positioned in the desired outflow location. In such embodiments, aqueous flows in the opposite direction as described above: aqueous enters the shunt 200 at the interior chamber 216 via the second port 208, flows through the lumen 206, and drains into the desired outflow location via the first port 207.

In some embodiments, the shunt 200 has a generally flat profile (e.g., as defined by the frame 210). For example, the frame 210 (the elongated portion 212, the bladder portion 214, or both the elongated portion 212 and the bladder portion 214) can have a longitudinal cross-sectional dimension (e.g., height, width, diameter, etc.) of about 100 μm or less, 90 μm or less, 80 μm or less, 70 μm or less, 60 μm or less, and/or 50 μm or less. In some embodiments, use of a rectangular or oval-shaped lumen 206 (as opposed to a circular lumen) may help decrease one or more dimensions of the shunt 200 without substantially affecting the therapy provided by the shunt 200. Without being bound by theory, reducing the one or more dimensions of the shunt 200 may help reduce and/or minimize damage to the eye during and after implanting the shunt 200 into the eye, which in turn may reduce the recovery time following the implant procedure and/or reduce side effects associated with the shunt. The overall shape "L" shape of the shunt 200 may also help anchor the shunt in position and prevent unwanted migration of the shunt 200 despite its relatively small profile.

The shunt 200 further includes a flow control assembly 220 (also referred to herein as an "actuation assembly") positioned in the interior chamber 216. The flow control assembly 220 can include an anchor 221, one or more actuation elements 222, and a lever or gating element 225. As will be described in greater detail below with reference to FIG. 2C, the flow control assembly 220 is configured to control the flow of fluid through the lumen 206 by selectively blocking and/or unblocking a portion of the lumen 206 that is in fluid communication with the interior chamber 216.

Figure 2C:
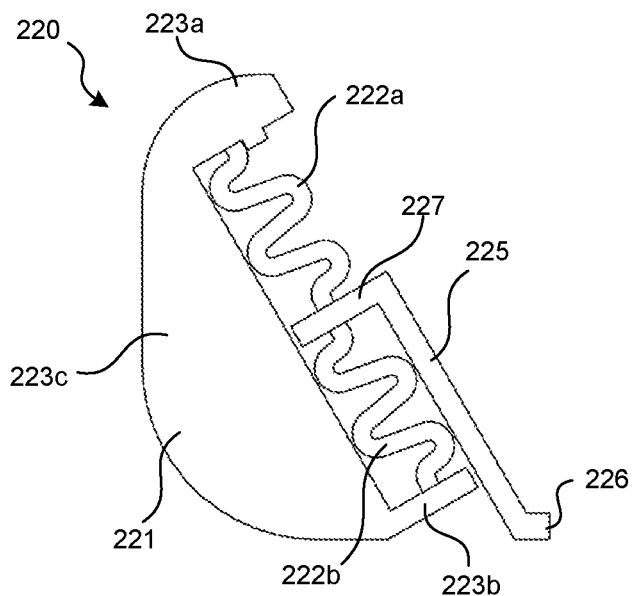

FIG. 2C is an enlarged view of the flow control assembly 220 depicted alone with other features of the shunt 200 (FIGS. 2A and 2B) omitted for purposes of illustration. As noted above, the flow control assembly 220 includes an anchor 221, actuation elements 222 (shown as a first actuation element 222a and a second actuation element 222b, and collectively referred to as the "actuation elements 222"), and a gating element 225. The anchor 221 is configured to secure the flow control assembly 220 in a desired position within the interior chamber 216. For example, the anchor 221 can conform to a portion of the interior chamber 216. In other embodiments, the anchor 221 can otherwise secure the flow control assembly 220 to the frame 210. The anchor 221 can also provide an anchoring element for the actuation elements 222. For example, the anchor 221 can include a first anchoring element 223a and a second anchoring element 223b extending from a body portion 223c of the anchor 221. The anchoring elements 223a and 223b can be integral with the body portion 223c or can be separate components otherwise secured to the body portion 223c. The anchoring elements 223a-223c remain generally static during operation of the actuation elements 222, described below.

The gating element 225 includes a first portion 227 (e.g., an "arm") positioned between the first actuation element 222a and the second actuation element 222b and a second portion 226 spaced apart from the first portion 225. The second portion 226 can be configured to at least partially block the lumen 206 and/or an aperture or orifice of the lumen 206 (thus at least partially blocking fluid from flowing out of the lumen 206 and into the interior chamber 216) in certain configurations, such as the configuration depicted in FIGS. 2A and 2B. Accordingly, the second portion 226 can also be referred to as a "blocking feature" or a "flow control element." The gating element 225 can have a generally elbow or "L" shape, although other configurations are possible.

The first actuation element 222a extends between the first anchoring element 223a and the first portion 227 of the gating element 225. The second actuation element 222b extends between the second anchoring element 223b and the first portion 227 of the gating element 225. The actuation elements 222 are configured to move the gating element 225 between a plurality of positions to control the flow of fluid through the shunt 200. For example, the first actuation element 222a and the second actuation element 222b can be composed of a shape memory material, such as a shape memory alloy (e.g., nitinol). Accordingly, the first actuation element 222a and the second actuation element 222b can be transitionable at least between a first material phase or state (e.g., a martensitic state, a R-phase, a composite state between martensitic and R-phase, etc.) and a second material phase or state (e.g., an austenitic state, an R-phase state, a composite state between austenitic and R-phase, etc.). In the first material state, the first actuation element 222a and the second actuation element 222b may be deformable (e.g., plastic, malleable, compressible, expandable, etc.). In the second material state, the first actuation element 222a and the second actuation element 222b may have a preference toward a specific preferred geometry (e.g., original geometry, manufactured geometry, heat set geometry, etc.). The first actuation element 222a and the second actuation element 222b can be transitioned between the first material state and the second material state by applying energy (e.g., heat) to the actuation elements to heat the actuation elements above a transition temperature. Energy can be applied to the actuation elements via an energy source positioned external to the body (e.g., a laser), RF heating, resistive heating, or the like. In some embodiments, the transition temperature for both the first actuation element 222a and the second actuation element 222b is above an average body temperature (e.g., an average temperature in the eye). Accordingly, both the first actuation element 222a and the second actuation element 222b are generally in the deformable first state when the shunt 200 is implanted in the body until they are actuated. If an actuation element (e.g., the first actuation element 222a) is deformed relative to its preferred geometry while in the first state, heating the actuation element (e.g., the first actuation element 222a) above its transition temperature causes the actuation element to transition to the second state and therefore move from the deformed shape to and/or toward its preferred geometry. In some embodiments, the first actuation element 222a can be selectively heated independently of the second actuation element 222b, and the second actuation element 222b can be selectively heated independently of the first actuation element 222a.

The first actuation element 222a and the second actuation element 222b generally act in opposition. For example, if the second actuation element 222b is deformed relative to its preferred geometry, actuation of the second actuation element 222b (e.g., heating the second actuation element 222b above its transition temperature) causes the second actuation element 222b to move toward its preferred geometry. This causes a corresponding deformation in the first actuation element 222a, which remains in the first material state and thus is generally malleable. For example, in the illustrated embodiment, the second actuation element 222b is compressed (e.g., shortened) relative to its preferred geometry. Heating the second actuation element 222b above its transition temperature causes the second actuation element 222b to straighten out (e.g., lengthen, expend, etc.) and move toward its preferred geometry. Because the second anchoring element 223b does not move as the second actuation element 222b changes shape, the first actuation element 222a (which is not heated and therefore in the first generally malleable state) is compressed to account for the shape change of the second actuation element 222b. This also moves the first portion 227 of the gating element 225 toward the first anchoring element 223a, which causes the second portion 226 of the gating element 225 to unblock and/or further unblock the lumen 206. This can increase flow through the lumen 206. The operation can be reversed by heating the first actuation element 222a above its transition temperature, which causes it to move (e.g., expand) toward its preferred geometry, which moves the first portion 227 of the gating element 225 back toward the second anchoring element 223b and the second portion 226 of the gating element 225 back into a blocking position. This can decrease flow through the lumen 206. Accordingly, the first actuation element 222a and the second actuation element 222b can be selectively and independently actuated to further block or unblock the lumen 206 to change the flow of fluid therethrough. In some embodiments, the gating element 225 can be moved to any number of positions between fully blocking and fully unblocking the lumen 206, and the flow control assembly 220 can be selectively adjusted after placement within the eye (e.g., via non-invasive energy) to provide a variety of different outflow resistance levels by incrementally adjusting the gating element 225 relative to the lumen 206. Additional details regarding the operation of flow control mechanisms generally similar to the flow control mechanism 220 are described below in Section D and with reference to FIGS. 5A-5D.

Figure 2D:
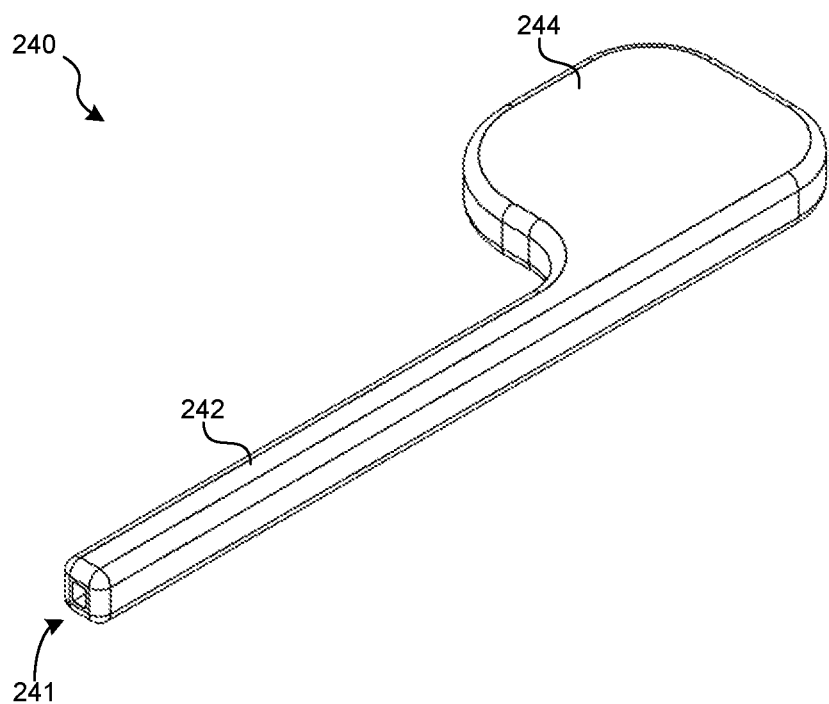
Figure 2E:
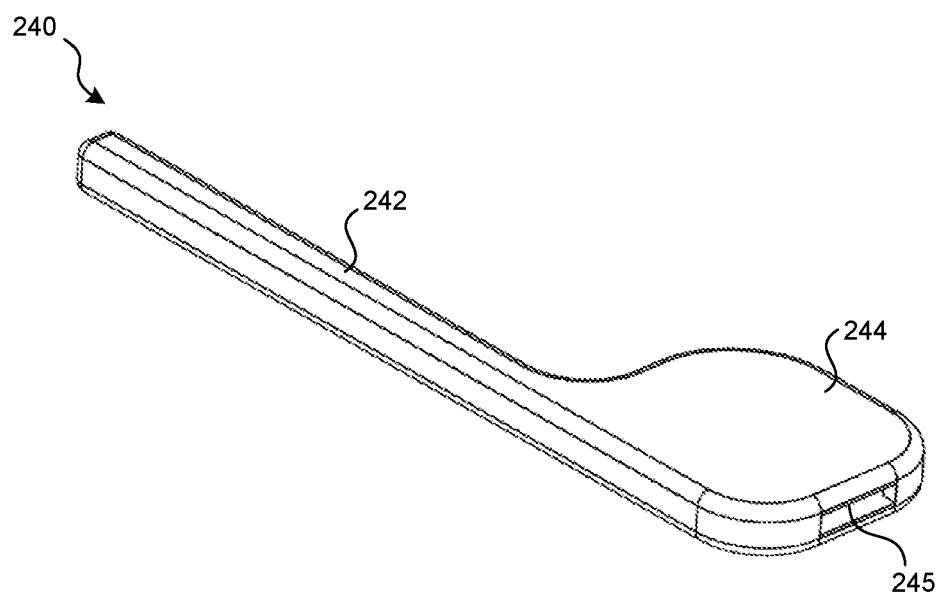

FIGS. 2D and 2E illustrate a cover 240 encasing the shunt 200. In some embodiments, the cover 240 is a thin protective membrane surrounding the frame 210. In other embodiments, the cover 240 is simply the outer surface of the frame 210. In embodiments in which the cover 240 is separate from the frame 210, the cover 240 includes an elongated portion 242 corresponding to the elongated portion 212 of the frame 210. The cover 240 also includes a bladder portion 244 corresponding to the bladder portion 214 of the frame 210. Referring to FIG. 2D, a first end portion (e.g., the proximal end portion) of the cover 240 has an opening 241 that aligns with the first port 207 to provide fluid access to lumen 206. As illustrated, the opening 241 can be rectangular to match the cross-section of the lumen 206. Referring to FIG. 2E, a second end portion (e.g., a distal end portion) of the cover 240 has an opening 245 that aligns with the second port 208 to permit fluid to flow out of the shunt 200. In embodiments in which the bladder portion 244 is positioned in the desired outflow location (e.g., the bleb space), the opening 245 directs fluid away from the globe of the eye and ensures that any growth in the bleb due to the outflow of fluid occurs in a direction away from the globe of the eye.

Figure 3A:
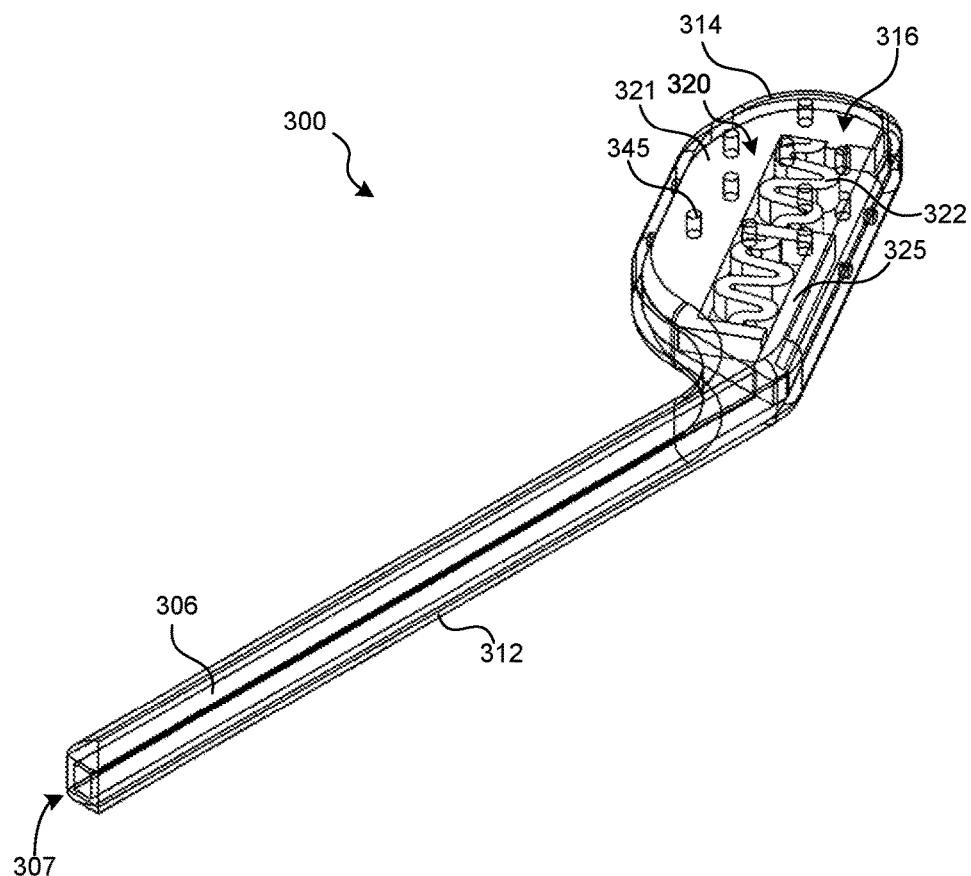
FIGS. 3A-3D illustrate another adjustable flow glaucoma shunt configured in accordance with select embodiments of the present technology.
Figure 3B:
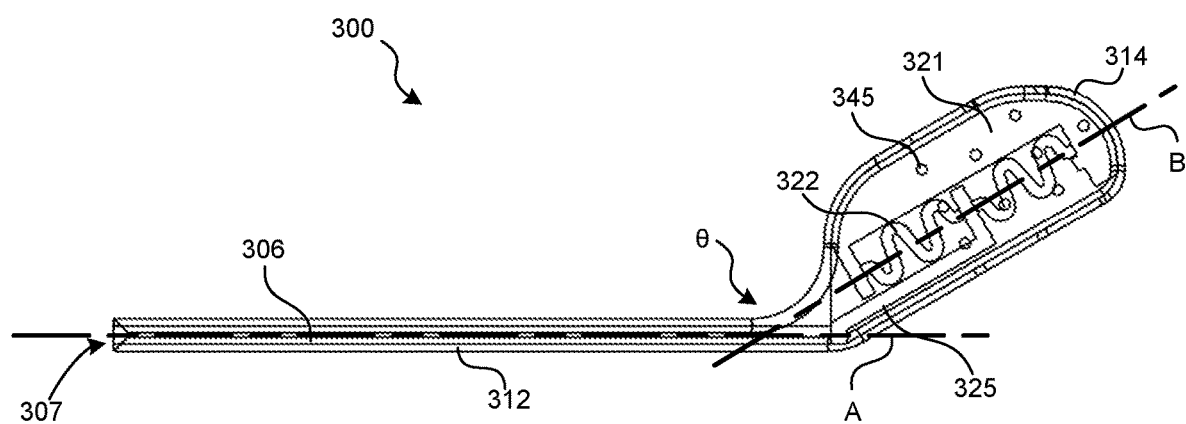
Figure 3C:
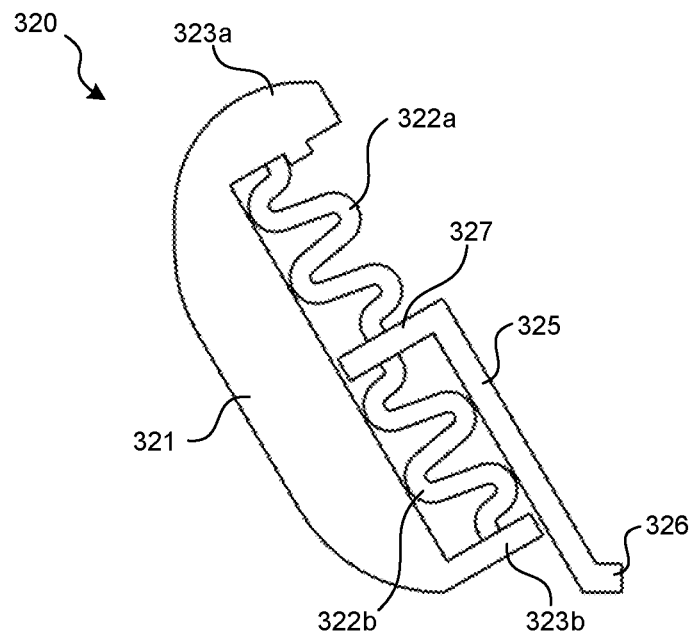
Figure 3D:
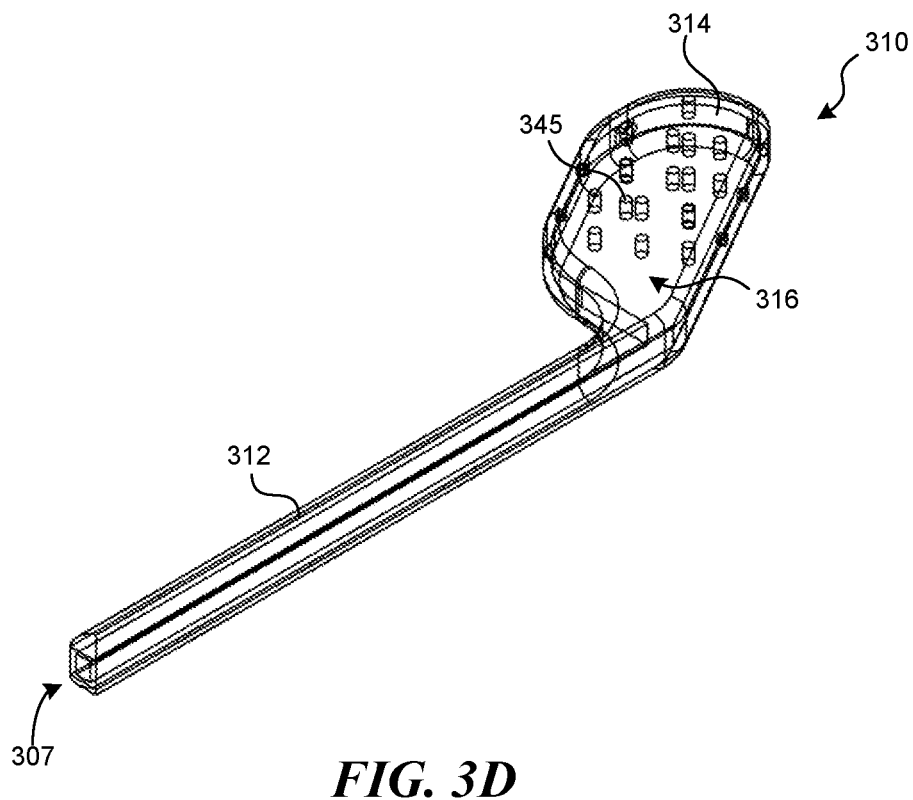

FIGS. 3A-3D illustrate an adjustable flow shunt 300 ("shunt 300") configured in accordance with select embodiments of the present technology. In particular, FIG. 3A is an isometric view of the shunt 300, FIG. 3B is a top view of the shunt 300, FIG. 3C is an enlarged view of a flow control assembly 320 of the shunt 300, and FIG. 3D is an isometric view of a frame 310 of the shunt 300. The shunt 300 can be similar to the shunt 200. For example, referring to FIGS. 3A and 3B, the shunt 300 includes a frame 310 having an elongated portion 312 and a bladder portion 314. The bladder portion 314 defines an interior chamber 316. A lumen 306 extends through the elongated portion 312 and is fluidly coupled to the interior chamber 316. The shunt 300 further includes a flow control assembly 320 having an anchor 321, actuation elements 322, and a gating element 325. Referring to FIG. 3C, the anchor 321 can include a first anchor element 323a, a second anchor element 323b, and a base portion 323c. The gating element 325 can include a first portion 327 and a second portion 326. The actuation elements 322 can include a first actuation element 322a extending between the first anchor element 323a and the first portion 327 of the gating element 325, and a second actuation element 322b extending between the second anchor element 232b and the first portion 327 of the gating element 325. The shunt 300, including the flow control assembly 320, can operate in a similar fashion as the shunt 200 described above with respect to FIGS. 2A-2D. The following description of the shunt 300 therefore focuses on features of the shunt 300 that are different than the shunt 200. However, one skilled in the art will appreciate that the description of like features for the shunt 200 apply to like features of the shunt 300.

Referring now to FIG. 3B, the frame 310 can be angled. For example, the longitudinal axis A of the elongated portion 312 can be non-parallel to the longitudinal axis B of the bladder portion. For example, the longitudinal axis A and the longitudinal axis B may form an angle θ between about 90 degrees and about 180 degrees, such as about 95 degrees, about 100 degrees, about 105 degrees, about 110 degrees, about 115 degrees, about 120 degrees, about 125 degrees, about 130 degrees, about 135 degrees, about 140 degrees, about 145 degrees, about 150 degrees, about 155 degrees, about 160 degrees, about 165 degrees, about 170 degrees, or about 175 degrees. In some embodiments, the angled or non-linear configuration of the frame 310 is expected to help secure the shunt 300 in a desired position. For example, the bend formed by the bladder portion 314 and the elongated portion 312 can act as a wedge to help prevent and/or reduce axial or lateral migration of the shunt 300.

Referring next to FIG. 3D, which illustrates the frame 310 with the flow control assembly 320 (FIGS. 2C) omitted for purposes of illustration, the frame 310 can also include a plurality of apertures 345 configured to fluidly connect the interior chamber 316 an environment external to the bladder portion 314. For example, when implanted within the eye, the bladder portion 314 can be positioned within a target outflow location, and the apertures 345 permit aqueous draining through the shunt 300 to exit the interior chamber 316 and flow into the bleb space. In some embodiments, the plurality of apertures 345 are positioned only on a medial and/or distal portion of the bladder portion 314 (relative to the elongated portion 312), with no apertures positioned on the proximal portion of the bladder portion 314 that is adjacent to the elongated portion 312. Such configuration directs aqueous draining through the apertures 345 away from the globe of eye and ensures any growth in the drainage bleb will also be away from the globe of the eye. Further, having a plurality of apertures 345 enables drainage of aqueous to continue even if one of the apertures 345 becomes blocked by tissue ingrowth or clotting. The plurality of apertures 345 can be in addition to or in lieu of a primary outflow drainage port. As described above with respect to FIGS. 2C and 2D, the shunt 300 can further include a cover and/or the frame's outer surface can comprise a material suitable for exposure to tissue. If the shunt 300 has a cover, the cover can include a plurality of holes configured to align with the plurality of apertures 345.

As one skilled in the art will appreciate, adjustable shunts configured in accordance with the present technology can include any combination of the above described features and are not limited to the specific embodiments illustrated herein. For example, while the elongated portion is depicted as intersecting with the bladder portion at a proximal corner of the bladder portion, the elongated portion can alternatively intersect the bladder portion at a central or other region of the bladder portion. Likewise, various components of the flow control assemblies described herein, such as the anchor, the actuation elements, and the gating element, can take any number of configurations without deviating from the scope of the present technology.

Although the shunts discussed above are primarily described as having the flow control assembly positioned at or adjacent an outflow end of the shunt, the flow control assemblies described herein can also be positioned at other positions along the length of the shunt. For example, the flow control assembly can be positioned near a proximate (e.g., inflow) end of the shunt and/or within an anterior chamber. Accordingly, the shunts described above in FIGS. 2A-3D can be oriented in multiple directions, depending on the desired arrangement (e.g., the shunts can be implanted with the flow control assembly proximate the anterior chamber or with the flow control assembly proximate the desired outflow location). In some embodiments, placing the flow control assembly in the anterior chamber is expected to reduce the amount of tissue interference with the non-invasive energy used to selectively adjust the flow control assembly. In embodiments in which the flow control assembly is positioned within the anterior chamber, the bladder portion of the outer membrane can also be positioned within the anterior chamber. When placed in the anterior chamber, the bladder portion can serve several similar functions to those described above. For example, the bladder portion can protect the flow control assembly and/or anchor the shunt. If the bladder portion is positioned around the flow control assembly in the anterior chamber, the shunts described herein can optionally have a second bladder surrounding the outflow end of the shunt. The second bladder can reduce backflow pressure through the shunt and/or help prevent tissue ingrowth in a bleb or other desired outflow location.

C. Methods of Manufacturing Flow Control Assemblies with Shape Memory Actuation Elements Aspects of the present technology are further directed to methods of manufacturing the devices described herein. As described herein, select embodiments of the present technology include a flow control assembly (e.g., the flow control assemblies 220 and 320 of the shunts 200 and 300, respectively) composed, at least in part, of a shape memory material such as nitinol. To manufacture such nitinol-based flow control assemblies, the desired shape of the flow control assembly can be fabricated (e.g., cut, such as laser cut) from a piece (e.g., sheet, strip, etc.) of nitinol. In some embodiments, the flow control assembly can be fabricated from a single piece of nitinol.

Figure 4A:
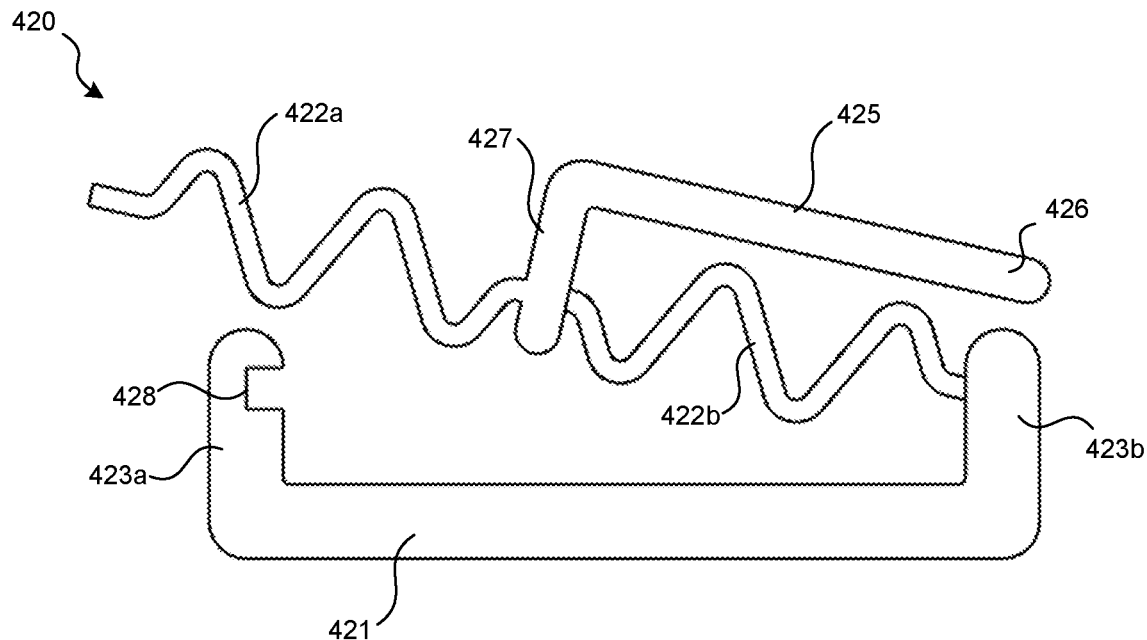
FIGS. 4A and 4B illustrate various stages of a flow control assembly during the manufacture of an adjustable flow glaucoma shunt configured in accordance with select embodiments of the present technology.
Figure 4B:
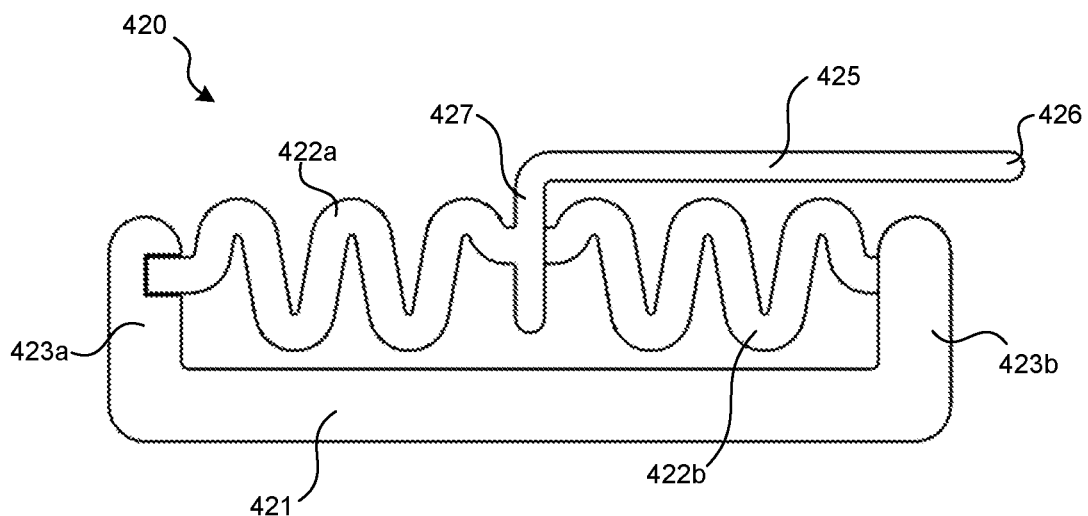

FIGS. 4A and 4B illustrate various stages of manufacture of a flow control assembly 420 (which can also be referred to herein as an "actuation assembly") fabricated from a piece (e.g., a sheet or strip) of nitinol or other suitable material in accordance with select embodiments of the present technology. More specifically, FIG. 4A illustrates a structure corresponding to the flow control assembly 420 after it has been cut from a sheet of nitinol (e.g., the "fabricated" or "cut" "configuration"), and FIG. 4B illustrates the flow control assembly 420 after it has been manipulated into an operational position (e.g., the "assembled" or "operational" configuration). As described below, in at least some embodiments the flow control assembly is fabricated as a unitary structure from a single piece of material. The flow control assembly 420 can include features generally similar to the features described above with respect to the flow control assemblies 220 and 320. For example, the flow control assembly 420 can include an anchor 421 having anchoring elements 423a and 423b. The flow control assembly 420 can also include actuation elements 422a and 422b and a gating element 425. As described above, the gating element 425 can include a first portion 427 and a second portion 426. In the illustrated embodiment, the flow control assembly 420 further includes a notch 428 in the first anchoring element 423a.

Referring to FIG. 4A, the illustrated embodiment shows the fabricated configuration of the flow control assembly before it has been formed into its operational configuration. As described above with respect to FIGS. 2C and 3C, the first actuation element 422a has a first end portion connected to the arm 427 and a second end portion spaced apart from the arm 427. In the fabricated configuration, the second end portion of the first actuation element 422a is free (i.e., the second end portion is not secured to the anchor 421 and/or the first anchoring element 423a) and both the first actuation element 422a and the second actuation element 422b are in their preferred geometry (e.g., their original, manufactured geometry). In some embodiments, the first actuation element 422a and the second actuation element 422b can have the same preferred geometry. In other embodiments, the first actuation element 422a and the second actuation element 422b can have different preferred geometries.

The fabricated configuration can be converted into the operational configuration by securing the second end portion of the first actuation element 422a (i.e., the free end) to the anchor 421 and/or the first anchoring element 423a. The process of securing the free end of the first actuation element 422a to the first anchoring element 423a deforms the first actuation element 422a and/or the second actuation element 422b relative to its preferred geometry (thereby "prestraining" and/or "prestressing" the first actuation element 422a and/or the second actuation element 422b). For example, in the embodiment illustrated in FIG. 4B, the first actuation element 422a and the second actuation element 422b can be bent or otherwise compressed such that the second end portion of the first actuation element 422a is positioned within the notch 428 of the first anchoring element 423a, thereby securing the flow control assembly 420 in the operational configuration. The first actuation element 422a and/or the second actuation element 422b are therefore at least partially bent, compressed, or otherwise deformed relative to their preferred geometry (shown in FIG. 4A) as they are placed into the operational configuration. In the operational configuration, the first actuation element 422a may exert a generally outward and/or upward force on the first anchoring element 423a to ensure that the first actuation element 422a remains in the notch 428 and that the flow control assembly 420 remains in the operational configuration. In some embodiments, the first actuation element 422a can be secured to the first anchoring element 423a by other means in addition to, or in lieu of, the outward and/or upward force generated by the first actuation element 422a.

For example, the first actuation element 422a can be welded, bonded, or otherwise secured to the first anchoring element 423a.

In some embodiments, the first actuation element 422a and/or the second actuation element 422b are stretched or otherwise lengthened when placing the flow control assembly 420 in the operational configuration. For example, in some embodiments the first anchoring element 423a may be spaced apart from the second anchoring element 423b by a length greater than a combined length of the first actuation element 422a and the second actuation element 422b in the fabricated configuration. Accordingly, to transform the flow control assembly 420 into the operational configuration, the first actuation element 422a and/or the second actuation element 422b can be stretched or lengthened relative to their preferred geometries. Once stretched, the first actuation element 422a can be secured to the first anchoring element 423a (e.g., via welding, bonding, or other suitable techniques) to hold the flow control assembly 420 in the operational configuration.

Once in the operational configuration, the flow control element 420 can be positioned within a shunt (e.g., inserted into an interior chamber, such as the interior chamber 216 or 316 described above respect to the shunts 200 and 300, respectively). In some embodiments, the geometry/topography of the anchor 421 conforms with a portion of the interior chamber such that the flow control assembly 421 is automatically anchored in position when positioned in the interior chamber. Alternatively or additionally, the flow control assembly 420 can be secured to the shunt using other anchoring techniques that do not substantially interfere with operation of the shunt. Once positioned within the shunt, the flow control assembly 420 can operate as described in Section D below with respect to FIGS. 5A-5D.

In some embodiments, the first actuation element 422a and/or the second actuation element 422b are optionally biased after placing the flow control assembly in the operational configuration. For example, the first actuation element 422a can be manipulated (e.g., using energy) such that is has a different length than the second actuation element 422b. In such embodiments, the first actuation element 422a is configured to retain its biased shape (e.g., the first actuation element 422a can be composed of a shape-memory material such as nitinol). Biasing at least one of the actuation elements before deployment of the shunt places the shunt in an "open" (e.g., permitting flow), partially "open", or "closed" (e.g., not permitting flow) position for the implant procedure. The biasing step can be done before or after placement of the flow control assembly 420 within the shunt.

Without being bound by theory, the above method of manufacturing the flow control assemblies described herein provides several advantages. For example, it enables the flow control assembly to be fabricated (e.g., cut) as a unitary structure from a single piece of material, which is expected to simplify the manufacturing process. As another example, because it is formed from a unitary structure, the flow control assemblies may have fewer coupled parts that could malfunction after being implanted into the patient, which may in at least some cases increase the life of the shunts described herein. However, as one skilled in the art will appreciate from the disclosure herein, the flow control assemblies described herein can be formed by methods other than those described above with respect to FIGS. 4A and 4B. For example, in embodiments wherein the flow control assemblies comprise nitinol, the flow control assemblies can be formed using any technique suitable for manipulating nitinol into the desired configuration. Accordingly, the present technology is not limited to the methods of manufacture expressly described herein. Rather, the shunts described herein can be manufactured using other suitable methods not expressly set forth herein.

D. Operation of Shape Memory Actuation Elements

As described above, the present technology is generally directed to implantable systems and devices for facilitating the flow of fluid between a first body region and a second body region. The devices generally include a drainage and/or shunting element having a lumen extending therethrough for draining or otherwise shunting fluid between the first and second body regions. Further, devices configured in accordance with the present technology may be selectively adjustable to control the amount of fluid flowing between the first and second body regions. In some embodiments, for example, the devices comprise a flow control assembly or actuation assembly that drives movement of a gating element to modulate flow resistance through the lumen, thereby increasing or decreasing the relative drainage rate of fluid between the first body region and the second body region.

In some embodiments of the present technology, the flow control assemblies (e.g., actuation assemblies, fluid resistors, etc.) comprise at least two actuation elements coupled to a moveable element (e.g., a gating element, an arm, etc.). The moveable element can be formed to interface with (e.g., at least partially block) a lumen and/or a lumen orifice. The orifice can be an inflow orifice or an outflow orifice. In other embodiments, the moveable element can be an intermediate element between the actuation element and a flow control element that interfaces with or otherwise engages a shunt lumen or orifice. In such embodiments, movement of the moveable element can adjust a geometry of the flow control element, which in turn adjusts a size, shape, or other dimension of a shunt lumen or orifice. Movement of the actuation elements generates (e.g., translational and/or rotational) movement of the moveable element.

The actuation element(s) can include a shape memory material (e.g., a shape memory alloy, or a shape memory polymer), and movement of the actuation element(s) can be generated through applied stress and/or use of a shape memory effect (e.g., as driven by a change in temperature). The shape memory effect enables deformations that have altered an element from its preferred geometric configuration (e.g., original configuration, shape-set configuration, heat-set configuration, etc.) to be largely or entirely reversed during operation of the flow control assembly. For example, thermal actuation (heating) can reverse deformation(s) by inducing a change in state (e.g., phase change) in the actuator material, inducing a temporary elevated internal stress that promotes a shape change toward the preferred geometric configuration. For a shape memory alloy, the change in state can be from a martensitic phase (alternatively, R-phase) to an austenitic phase. For a shape memory polymer, the change in state can be via a glass transition temperature or a melting temperature. The change in state can reverse deformation(s) of the material—for example, deformation with respect to its preferred geometric configuration—without any (e.g., externally) applied stress to the actuation element. That is, a deformation that is present in the material at a first temperature (e.g., body temperature) can be (e.g., thermally) recovered and/or altered by raising the material to a second (e.g., higher) temperature. Upon cooling (and changing state, e.g., back to martensitic phase), the actuation element retains its preferred geometric configuration. With the material in this relatively cooler-temperature condition it may require a lower force or stress to thermoelastically deform the material, and any subsequently applied external stress can cause the actuation element to once again deform away from the preferred geometric configuration.

The actuation element(s) can be processed such that a transition temperature at which the change in state occurs (e.g., the austenite start temperature, the austenite final temperature, etc.) is above a threshold temperature (e.g., body temperature). For example, the transition temperature can be set to be about 45 deg. C., about 50 deg. C., about 55 deg. C., or about 60 deg. C. In some embodiments, the actuator material is heated from body temperature to a temperature above the austenite start temperature (or alternatively above the R-phase start temperature) such that an upper plateau stress (e.g., "UPS_body temperature") of the material in a first state (e.g., thermoelastic martensitic phase, or thermoelastic R-phase at body temperature) is lower than an upper plateau stress (e.g., "UPS_actuated temperature") of the material in a heated state (e.g., superelastic state), which achieves partial or full free recovery. For example, the actuator material can be heated such that UPS_actuated temperature>UPS_body temperature. In some embodiments, the actuator material is heated from body temperature to a temperature above the austenite start temperature (or alternatively above the R-phase start temperature) such that an upper plateau stress of the material in a first state (e.g., "thermoelastic martensite or thermoelastic R-phase at body temperature") is lower than a lower plateau stress (e.g., "LPS") of the material in a heated state (e.g., superelastic state), which achieves partial or full free recovery. For example, the actuator material can be aged such that LPS_activated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase) is higher than a lower plateau stress of the material in a heated state, which achieves partial free recovery. For example, the actuator material can be aged such that LPS_activated temperature<UPS_body temperature.

The flow control assembly can be formed such that the actuation elements have substantially the same preferred geometric configuration (e.g., memory shape, or length, $L_0$). The flow control assembly can be assembled such that, upon introduction into a patient (e.g., implantation), at least one (e.g., a first) actuation element/shape memory element has been deformed with respect to its preferred geometric configuration (e.g., to have $L_1 \neq L_0$), while at least one other opposing (e.g., a second) actuation element/shape memory element positioned adjacent to the first actuation element is substantially at its preferred geometric configuration (e.g., $L_0$). In other embodiments, however, both the first and second actuation elements may be deformed with respect to their corresponding preferred geometric configurations upon introduction into the patient (e.g., the first actuation element is contracted relative to its preferred geometric configuration and the second actuation element is expanded relative to its preferred geometric configuration).

In some embodiments of the present technology, $L_1 > L_0$—for example, the deformed first actuation element is elongated with respect to its preferred "shape memory: length. In some embodiments, $L_1 < L_0$—for example, the deformed first actuation element is compressed with respect to its preferred shape memory length. The flow control assembly can be formed such that, in operation, its overall dimension (e.g., overall length) is substantially fixed (e.g., $L_0 + L_1 =$ a constant). For example, (e.g., outermost) ends of the actuation elements can be fixed, such that movement of the actuation elements occurs between the points of fixation. The overall geometry of the actuation elements, along with the lengths, can be selected such that, in operation, deformation within the actuation elements remains below about 10%, about 9%, about 8%, about 7%, or about 6%.

The (e.g., first and second) actuation elements are arranged such that a movement (e.g., deflection or deformation) of the first actuation element/first shape memory element is accompanied by (e.g., causes) an opposing movement of the second actuation element/second shape memory element. The movement can be a deflection or a deformation. In operation, selective heating of the first actuation element of the flow control assembly causes it to move to and/or toward its preferred geometric configuration (e.g., revert from $L_1$ to $L_0$), moving the coupled moveable element. At the same time, the elongation of the first actuation element is accompanied by (e.g., causes) a compression of the second actuation element (e.g., from $L_0$ to $L_1$). The second actuation element is not heated (e.g., remains at body temperature), and therefore the second actuation element deforms (e.g., remains martensitic and compresses). The first actuation element cools following heating, and returns to a state in which it can be plastically deformed. To reverse the configuration of the flow control assembly (e.g., the position of the moveable element), the second actuation element is heated to move to and/or toward its preferred geometric configuration (e.g., from $L_1$ to $L_0$). The return of the second actuation element to its preferred geometric configuration causes the moveable element to move back to its prior position, and compresses the first actuation element (e.g., from $L_0$ to $L_1$). The position of the moveable element for the flow control assembly can be repeatably toggled (e.g., between open and closed) by repeating the foregoing operations. The heating of an actuation element can be accomplished via application of incident energy (e.g., via a laser or inductive coupling). Further, as mentioned above, the source of the incident energy may be external to the patient (e.g., non-invasive).

FIGS. 5A-5D schematically illustrate operation of a flow control assembly 500 for use with an adjustable flow shunt and configured in accordance with select embodiments of the present technology. Although the flow control assembly 500 is shown schematically, one skilled in the art will appreciate that the principles and modes of operation discussed with respect to the flow control assembly 500 can apply to any of the flow control assemblies disclosed herein. Accordingly, the flow control assembly 500 can be generally similar to and/or the same as the flow control assemblies 220, 320, and 420 previously described.

Referring collectively to FIGS. 5A-5D, the flow control assembly 500 can include a first actuation element 501 and a second actuation element 502, which can be generally similar to the actuation elements described previously with respect to FIGS. 2A-4B. The first actuation element 501 can extend between the gating element 503 and a first anchoring element 504. The second actuation element 502 can extend between the gating element 503 and a second anchoring element 505. The first anchoring element 504 and the second anchoring element 505 can be secured to a generally static component of the shunt (not shown). In other embodiments, the first anchoring element 504 and/or the second anchoring element 505 can be omitted and the first actuation element 501 and/or the second actuation element 502 can be secured directly to a portion of the device or system for shunting fluid (not shown). In any of these embodiments, selectively modifying fluid flow through the shunt by moving the gating element 503 occurs without damaging or otherwise negatively affecting tissue of the patient.

The first actuation element 501 and the second actuation element 502 can be composed of a shape memory material, such as a shape memory alloy (e.g., nitinol). Accordingly, the first actuation element 501 and the second actuation element 502 can be transitionable between a first material phase or state (e.g., a martensitic material state, an R-phase material state, etc.) and a second material phase or state (e.g., an austenitic material state, an R-phase material state, etc.). In the first state, the first actuation element 501 and the second actuation element 502 may be deformable (e.g., plastic, malleable, compressible, expandable, etc.). In the second state, the first actuation element 501 and the second actuation element 502 may have a preference toward a specific preferred geometry (e.g., original geometry, manufactured geometry, heat set geometry, etc.). The first actuation element 501 and the second actuation element 502 can be transitioned between the first state and the second state by applying energy (e.g., heat) to the actuation elements to heat the actuation elements above a transition temperature. In some embodiments, the transition temperature for both the first actuation element 501 and the second actuation element 502 is above an average body temperature (e.g., an average temperature in the eye). Accordingly, both the first actuation element 501 and the second actuation element 502 are typically in the deformable first state when the flow control assembly 500 is implanted in the body until they are heated (e.g., actuated).

If an actuation element (e.g., the first actuation element 501) is deformed relative to its preferred geometry while in the first state, heating the actuation element (e.g., the first actuation element 501) above its transition temperature causes the actuation element to transition to the second state and therefore transition from the deformed shape to and/or toward its preferred geometry. Heat can be applied to the actuation elements via an energy source positioned external to the body (e.g., a laser), RF heating, resistive heating, or the like. In some embodiments, the first actuation element 501 can be selectively heated independently of the second actuation element 502, and the second actuation element 502 can be selectively heated independently of the first actuation element 501.

Figure 5A:
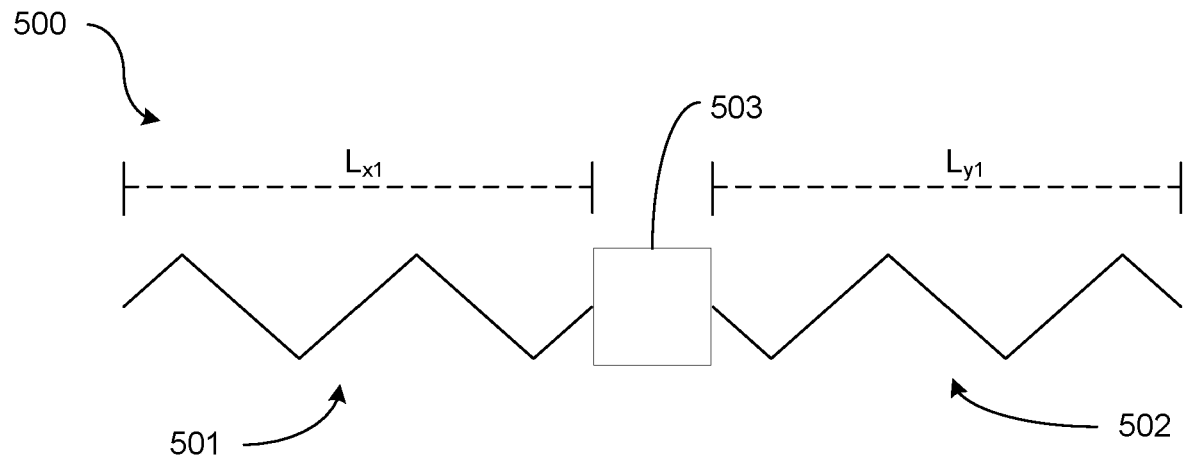
FIGS. 5A-5D illustrate a flow control assembly configured in accordance with embodiments of the present technology.

Referring to FIG. 5A, the first actuation element 501 and the second actuation element 502 are shown in a state before being secured to the first and second anchoring elements. In particular, the first actuation element 501 and the second actuation element 502 are in their unbiased preferred geometries. In the illustrated embodiment, the first actuation element 501 has an original shape having a length $L_{x1}$, and the second actuation element 502 has an original shape having a length $L_{y1}$. In some embodiments, $L_{x1}$ is equal to $L_{y1}$. In other embodiments, $L_{x1}$ is less than or greater than (i.e., not equal to) $L_{y1}$.

Figure 5B:
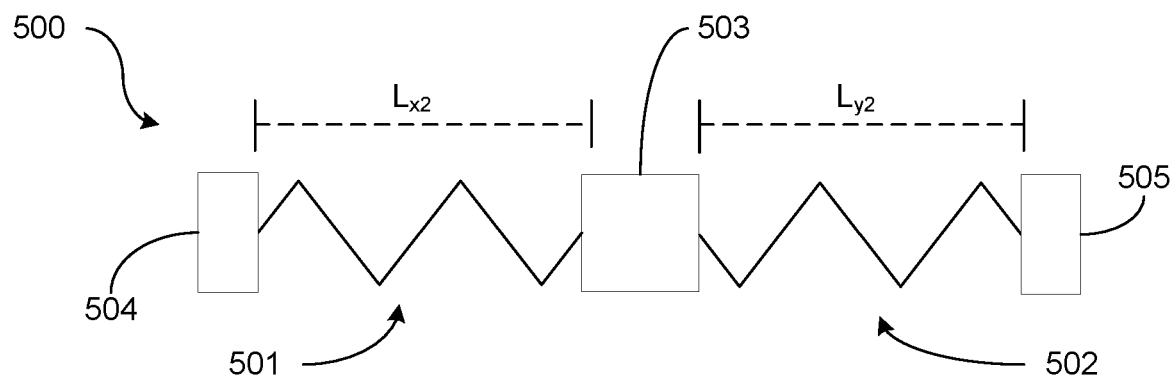

FIG. 5B illustrates the flow control assembly 500 in a first (e.g., assembled or operational) configuration after the first actuation element 501 has been secured to the first anchoring element 504, and the second actuation element 502 has been secured to the second anchoring element 505. In the first configuration, both the first actuation element 501 and the second actuation element 502 are at least partially deformed (e.g., prestressed and/or prestrained) relative to their preferred geometries. For example, the first actuation element 501 is compressed (e.g., shortened) relative to its preferred geometry (FIG. 5A) such that it assumes a second length $L_{x2}$ that is less than the first length $L_{x1}$. Likewise, the second actuation element 502 is also compressed (e.g., shortened)

relative to its preferred geometry (FIG. 5A) such that it assumes a second length $L_{y2}$ that is less than the first length $L_{y1}$. In the illustrated embodiment, $L_{x1}$ is equal to $L_{y1}$, although in other embodiments $L_{x1}$ can be less than or greater than (i.e., not equal to) $L_{y1}$. In other embodiments, the first actuation element 501 and/or the second actuation element 502 are stretched (e.g., lengthened) relative to their preferred geometries before being secured to the anchoring elements. For example, in some embodiments both the first actuation element 501 and the second actuation element 502 are stretched relative to their preferred geometries. In other embodiments, the first actuation element 501 is compressed (e.g., shortened) relative to its preferred geometry and the second actuation element 502 is stretched (e.g., lengthened) relative to its preferred geometry. In some embodiments, only one of the actuation elements (e.g., the first actuation element 501) is deformed relative to its preferred geometry, and the other actuation element (e.g., the second actuation element 502) retains its preferred geometry.

Figure 5C:
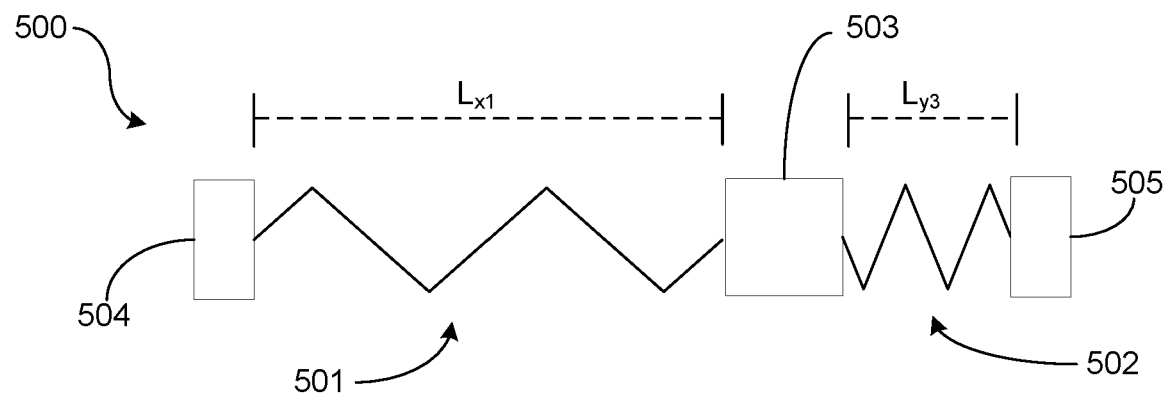

FIG. 5C illustrates the flow control assembly 500 in a second configuration different than the first configuration. In particular, in the second configuration, the flow control assembly 500 has been actuated relative to the first configuration shown in FIG. 5B to transition the first actuation element 501 from the first (e.g., martensitic) state to the second (e.g., austenitic) state. Because the first actuation element 501 was deformed (e.g., compressed) relative to its preferred geometry while in the first configuration, heating the first actuation element 501 above its transition temperature causes the first actuation element 501 to move to and/or toward its preferred geometry having a length $L_{x1}$ (FIG. 5A). As described above, the first anchoring element 504 and the second anchoring element 505 are fixedly secured to a generally static structure (e.g., such that a distance between the first anchoring element 504 and the second anchoring element 505 does not change during actuation of the first actuation element 501). Accordingly, as the first actuation element 501 increases in length toward its preferred geometry, the second actuation element 502, which is unheated and therefore remains in the generally deformable (e.g., martensitic) state, is further compressed to a length $L_{y3}$ that is less than $L_{y1}$ and $L_{y2}$. In the illustrated embodiment, this moves the gating element 503 away from the first anchoring element 504 and toward the second anchoring element 505.

Figure 5D:
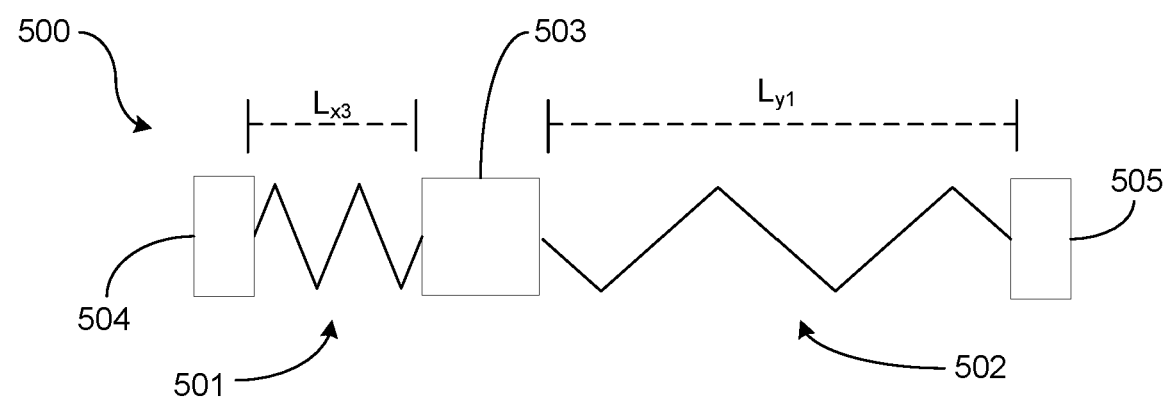

FIG. 5D illustrates the flow control assembly 500 in a third configuration different than the first configuration and the second configuration. In particular, in the third configuration the flow control assembly 500 has been actuated relative to the second configuration shown in FIG. 5C to transition the second actuation element 502 from the first (e.g., martensitic) state to the second (e.g., austenitic) state. Because the second actuation element 502 was deformed (e.g., compressed) relative to its original shape while in the second configuration, heating the second actuation element 502 above its transition temperature causes the second actuation element 502 to move to and/or toward its preferred geometry having a length $L_{y1}$ (FIG. 5A). As described above, the first anchoring element 504 and the second anchoring element 505 are fixedly secured to a generally static structure (e.g., such that the distance between the first anchoring element 504 and the second anchoring element 505 does not change during actuation of the second actuation element 502). Accordingly, as the second actuation element 502 increases in length toward its preferred geometry, the first actuation element 501, which is unheated and therefore remains in the generally deformable (e.g., martensitic) state, is further deformed (e.g., compressed) relative to its original shape to a length $L_{x3}$ that is less than $L_{x1}$ and $L_{x2}$. In the illustrated embodiment, this moves the gating element 503 away from the second anchoring element 505 and toward the first anchoring element 504 (e.g., generally opposite the direction the gating element 503 moves when the first actuation element 501 is actuated).

The flow control assembly 500 can be repeatedly transitioned between the second configuration and the third configuration. For example, the flow control assembly 500 can be returned to the second configuration from the third configuration by heating the first actuation element 501 above its transition temperature once the second actuation element 502 has returned to the deformable first state (e.g., by allowing the second actuation element 502 to cool below the transition temperature). Heating the first actuation element 501 above its transition temperature causes the first actuation element 501 to move to and/or toward its preferred geometry, which in turn pushes the gating element 503 back toward the second anchoring element 505 and transitions the flow control assembly 500 to the second configuration (FIG. 5C). Accordingly, the flow control assembly 500 can be selectively transitioned between a variety of configurations by selectively actuating either the first actuation element 501 or the second actuation element 502. After actuation, the flow control assembly 500 can be configured to substantially retain the given configuration until further actuation of the opposing actuation element. In some embodiments, the flow control assembly 500 can be transitioned to intermediate configurations between the second configuration and the third configuration (e.g., the first configuration) by heating a portion of the first actuation element 501 or the second actuation element 502.

As provided above, heat can be applied to the actuation elements via an energy source positioned external to the body (e.g., a laser), RF heating, resistive heating, or the like. In some embodiments, an external device (e.g., external device 220) directs the energy source to heat the one or more of the actuation elements based on readings from one or more sensors (e.g., sensor 210). In other embodiments, a user (e.g., a physician) operates the energy source to heat one or more of the actuation elements based on readings from one or more sensors. In some embodiments, the first actuation element 501 can be selectively heated independently of the second actuation element 502, and the second actuation element 502 can be selectively heated independently of the first actuation element 501. For example, in some embodiments, the first actuation element 501 is on a first electrical circuit and/or responds to a first frequency range for selectively and resistively heating the first actuation element 501 and the second actuation element 502 is on a second electrical circuit and/or responds to a second frequency range for selectively and resistively heating the second actuation element 502. As described in detail above, selectively heating the first actuation element 501 moves the gating element 503 in a first direction and selectively heating the second actuation element 502 moves the gating element 503 in a second direction generally opposite the first direction. The flow control assembly 500 can therefore be adjusted to achieve any of the operations described herein with respect to adjustable shunts.

As one of skill in the art will appreciate from the disclosure herein, various components of the shunting systems and devices described herein can be omitted without deviating from the scope of the present technology. Likewise, additional components not explicitly described above may be added to the systems and devices described herein without deviating from the scope of the present technology. Accordingly, the present technology is not limited to those the configurations expressly identified herein, but rather encompasses variations and alterations of the described embodiments.

E. Examples

Several aspects of the present technology are set forth in the following examples:

1. A method of manufacturing an adjustable flow shunt having a shunt and a flow control assembly, the method comprising:
fabricating a structure corresponding to the flow control assembly from a unitary piece of material, wherein the structure includes an anchoring element, an actuation element, and a gating element, and wherein the actuation element has a first end portion extending from the gating element and a second end portion not connected to another portion of the structure;
securing the second end portion of the actuation element to the anchoring element to form the flow control assembly; and
coupling the assembled flow control assembly to the shunt such that the flow control assembly is configured to at least partially control the flow of fluid through the shunt.

2. The method of example 1 wherein the anchoring element includes a notch, and wherein securing the second end portion of the actuation element to the anchoring element comprises positioning the second end portion of the actuation element into the notch.

3. The method of example 1 wherein securing the second end portion of the actuation element to the anchoring element comprises welding or bonding the second end portion of the actuation element to the anchoring element.

4. The method of any of examples 1-3 wherein securing the second end portion of the actuation element to the anchoring element includes at least partially deforming the actuation element relative to its fabricated geometry.

5. The method of example 4 wherein at least partially deforming the actuation element relative to its fabricated geometry includes prestressing and/or prestraining the actuation element.

6. The method of example 4 or 5 wherein at least partially deforming the actuation element includes compressing the actuation element.

7. The method of example 4 or 5 wherein at least partially deforming the actuation element includes lengthening the actuation element.

8. The method of any of examples 1-7 wherein fabricating the structure corresponding to the flow control assembly from the single piece of material includes laser cutting the structure from the single piece of material.

9. The method of any of examples 1-8 wherein the single piece of material is a sheet of nitinol and/or a strip of nitinol.

10. The method of any of examples 1-9 wherein the actuation element is a first actuation element, and wherein the structure further includes a second actuation element that, after the fabricating step, has a first end portion coupled to the anchoring element and a second end portion coupled to the gating element.

11. The method of example 10 wherein securing the second end portion of the first actuation element to the anchoring element includes at least partially deforming both the first actuation element and the second actuation element relative to their fabricated geometries.

12. The method of any of examples 1-11, further comprising biasing the actuation element before coupling the assembled flow control assembly to the shunt.

13. The method of any of examples 1-12 wherein coupling the assembled flow control assembly to the shunt includes positioning the flow control assembly within a frame.

14. A method of manufacturing a flow control assembly for use with an implantable medical device, the method comprising:
cutting a unitary structure corresponding to the flow control assembly from a sheet of nitinol and/or a strip of nitinol, wherein the unitary structure includes an anchoring element, one or more actuation elements, and a gating element, and wherein, once cut from the sheet and/or strip of nitinol, the actuation element has a first geometry; and
securing a free end of the actuation element to the anchoring element to form the flow control assembly, wherein securing the free end of the actuation element to the anchoring element deforms the actuation element such that it has a second geometry different than the first geometry.

15. The method of example 14 wherein securing the free end of the actuation element to the anchoring element includes compressing the actuation element.

16. The method of example 14 wherein securing the free end of the actuation element to the anchoring element includes lengthening the actuation element.

17. The method of example 14 wherein the first geometry has a greater length than the second geometry.

18. The method of example 14 wherein the first geometry has a shorter length than the second geometry.

19. The method of any of examples 14-18 wherein the actuation element is a first actuation element, and wherein the unitary structure further includes a second actuation element that, once cut from the sheet and/or strip of nitinol, has a third geometry.

20. The method of example 19 wherein the third geometry is different than the first geometry.

21. The method of example 19 wherein the third geometry is the same as the first geometry.

22. The method of any of examples 19-21 wherein securing the free end of the actuation element to the anchoring element at least partially deforms the second actuation element such that it has a fourth geometry different than the third geometry.

23. The method of example 22 wherein the fourth geometry is different than the second geometry.

24. The method of example 22 wherein the fourth geometry is the same as the second geometry.

23. A method of manufacturing a flow control assembly for use with an implantable medical device, comprising:
fabricating a unitary structure corresponding to a flow control assembly, wherein the unitary structure includes an anchoring element, one or more actuation elements, and a gating element, and wherein, once fabricated, the actuation element has a first geometry; and
securing a free end of the actuation element to the anchoring element to form the flow control assembly, wherein securing the free end of the actuation element to the anchoring element deforms the actuation element such that it has a second geometry different than the first geometry.

24. The method of example 23 wherein securing the free end of the actuation element to the anchoring element includes prestressing and/or prestraining the actuation element.

25. The method of example 23 or 24 wherein securing the free end of the actuation element to the anchoring element includes compressing the actuation element.

26. The method of example 23 or 24 wherein securing the free end of the actuation element to the anchoring element includes lengthening the actuation element.

27. The method of any of examples 23-26 wherein the actuation element is a first actuation element, and wherein the unitary structure further includes a second actuation element that, once fabricated, has a third geometry.

28. The method example 27 wherein securing the free end of the actuation element to the anchoring element at least partially deforms the second actuation element such that it has a fourth geometry different than the third geometry.

29. An adjustable flow shunt for treatment of glaucoma in a patient, the adjustable flow shunt comprising:
   a frame having a generally flat profile including—
      an elongated portion having a lumen extending therethrough, and
      a bladder portion defining an interior chamber, wherein the lumen is fluidly coupled to the interior chamber via an aperture; and
   a flow control assembly positioned within the interior chamber, the flow control assembly including—
      a gating element transitionable between a first position in which the gating element at least partially blocks the aperture and a second position in which the gating element does not blocking the aperture and/or blocks less of the aperture than in the first position, and
      an actuation element operably coupled to the gating element, wherein the actuation element is composed of a shape memory material and is configured to transition the gating element from the first position to and/or toward the second position.

30. The adjustable flow shunt of example 29 wherein the actuation element is a first actuation element, and wherein the flow control assembly further includes a second actuation element, wherein the second actuation element is composed of a shape memory material and is configured to transition the gating element from the second position to and/or toward the first position.

31. The adjustable flow shunt of example 29 or 30 wherein the flow control assembly further includes an anchoring element designed to conform to a portion of the interior chamber to thereby secure the flow control assembly within the interior chamber.

32. The adjustable flow shunt of example 31 wherein the actuation element, the gating element, and the anchoring element form a unitary structure formed from a single sheet of material.

33. The adjustable flow shunt of any of examples 29-32 wherein the lumen has a rectangular cross-sectional shape.

34. The adjustable flow shunt of any of examples 29-33 wherein the frame has a longitudinal cross-sectional dimension of less than about 100 μm.

35. The adjustable flow shunt of any of examples 29-33 wherein the frame has a longitudinal cross-sectional dimension of less than about 80 μm.

36. The adjustable flow shunt of any of examples 29-33 wherein the frame has a longitudinal cross-sectional dimension of less than about 60 μm.

37. The adjustable flow shunt of any of examples 29-36 wherein the bladder portion includes a first longitudinal axis extending therethrough and the elongated portion includes a second longitudinal axis extending therethrough, and wherein the first longitudinal axis is not parallel to the second longitudinal axis.

38. The adjustable flow shunt of example 37 wherein the first longitudinal axis and the second longitudinal axis form an angle between about 90 degrees and about 180 degrees.

39. The adjustable flow shunt of any of examples 29-38 wherein the flow control assembly is at least partially composed of nitinol.

40. The adjustable flow shunt of any of examples 29-39 wherein the bladder portion includes a plurality of holes.

Conclusion

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the adjustable flow shunts described herein may be combined with any of the features of the other adjustable flow shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with adjustable flow shunts have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of manufacturing an adjustable flow shunt having a shunt and a flow control assembly, the method comprising:
   fabricating a structure corresponding to the flow control assembly from a unitary piece of material, wherein the structure includes an anchoring element, an actuation element, and a gating element, and wherein the actuation element has a first end portion extending from the gating element and a second end portion not connected to another portion of the structure;

securing the second end portion of the actuation element to the anchoring element to form the flow control assembly; and coupling the assembled flow control assembly to the shunt such that the flow control assembly is configured to at least partially control the flow of fluid through the shunt.

2. The method of claim 1 wherein the anchoring element includes a notch, and wherein securing the second end portion of the actuation element to the anchoring element comprises positioning the second end portion of the actuation element into the notch.

3. The method of claim 1 wherein securing the second end portion of the actuation element to the anchoring element comprises welding or bonding the second end portion of the actuation element to the anchoring element.

4. The method of claim 1 wherein securing the second end portion of the actuation element to the anchoring element includes at least partially deforming the actuation element relative to its fabricated geometry.

5. The method of claim 4 wherein at least partially deforming the actuation element relative to its fabricated geometry includes prestressing and/or prestraining the actuation element.

6. The method of claim 4 wherein at least partially deforming the actuation element includes compressing the actuation element.

7. The method of claim 4 wherein at least partially deforming the actuation element includes lengthening the actuation element.

8. The method of claim 1 wherein fabricating the structure corresponding to the flow control assembly from the single piece of material includes laser cutting the structure from the single piece of material.

9. The method of claim 1 wherein the single piece of material is a sheet of nitinol and/or a strip of nitinol.

10. The method of claim 1 wherein the actuation element is a first actuation element, and wherein the structure further includes a second actuation element that, after the fabricating step, has a first end portion coupled to the anchoring element and a second end portion coupled to the gating element.

11. The method of claim 10 wherein securing the second end portion of the first actuation element to the anchoring element includes at least partially deforming both the first actuation element and the second actuation element relative to their fabricated geometries.

12. The method of claim 1, further comprising biasing the actuation element before coupling the assembled flow control assembly to the shunt.

13. The method of claim 1 wherein coupling the assembled flow control assembly to the shunt includes positioning the flow control assembly within a frame.

14. A method of manufacturing a flow control assembly for use with an implantable medical device, the method comprising:

cutting a unitary structure corresponding to the flow control assembly from a sheet of nitinol and/or a strip of nitinol, wherein the unitary structure includes an anchoring element, one or more actuation elements, and a gating element, and wherein, once cut from the sheet and/or strip of nitinol, the actuation element has a first geometry; and securing a free end of the actuation element to the anchoring element to form the flow control assembly, wherein securing the free end of the actuation element to the anchoring element deforms the actuation element such that it has a second geometry different than the first geometry.

15. The method of claim 14 wherein securing the free end of the actuation element to the anchoring element includes compressing the actuation element.

16. The method of claim 14 wherein securing the free end of the actuation element to the anchoring element includes lengthening the actuation element.

17. The method of claim 14 wherein the first geometry has a greater length than the second geometry.

18. The method of claim 14 wherein the first geometry has a shorter length than the second geometry.

19. The method of claim 14 wherein the actuation element is a first actuation element, and wherein the unitary structure further includes a second actuation element that, once cut from the sheet and/or strip of nitinol, has a third geometry.

20. The method of claim 19 wherein the third geometry is different than the first geometry.

21. The method of claim 19 wherein the third geometry is the same as the first geometry.

22. The method of claim 19 wherein securing the free end of the actuation element to the anchoring element at least partially deforms the second actuation element such that it has a fourth geometry different than the third geometry.

23. The method of claim 22 wherein the fourth geometry is different than the second geometry.

24. The method of claim 22 wherein the fourth geometry is the same as the second geometry.

25. A method of manufacturing a flow control assembly for use with an implantable medical device, comprising:

fabricating a unitary structure corresponding to a flow control assembly, wherein the unitary structure includes an anchoring element, one or more actuation elements, and a gating element, and wherein, once fabricated, the actuation element has a first geometry; and securing a free end of the actuation element to the anchoring element to form the flow control assembly, wherein securing the free end of the actuation element to the anchoring element deforms the actuation element such that it has a second geometry different than the first geometry.

26. The method of claim 25 wherein securing the free end of the actuation element to the anchoring element includes prestressing and/or prestraining the actuation element.

27. The method of claim 25 wherein securing the free end of the actuation element to the anchoring element includes compressing the actuation element.

28. The method of claim 25 wherein securing the free end of the actuation element to the anchoring element includes lengthening the actuation element.

29. The method of claim 25 wherein the actuation element is a first actuation element, and wherein the unitary structure further includes a second actuation element that, once fabricated, has a third geometry.

30. The method of claim 29 wherein securing the free end of the actuation element to the anchoring element at least partially deforms the second actuation element such that it has a fourth geometry different than the third geometry.

31. An adjustable flow shunt for treatment of glaucoma in a patient, the adjustable flow shunt comprising:

a frame having a generally flat profile including—
an elongated portion having a lumen extending therethrough, and a bladder portion defining an interior chamber, wherein the lumen is fluidly coupled to the interior chamber via an aperture; and a flow control assembly positioned within the interior chamber, the flow control assembly including— a gating element transitionable between a first position in which the gating element at least partially blocks the aperture and a second position in which the gating element does not blocking the aperture and/or blocks less of the aperture than in the first position, and an actuation element operably coupled to the gating element, wherein the actuation element is composed of a shape memory material and is configured to transition the gating element from the first position to and/or toward the second position.

32. The adjustable flow shunt of claim 31 wherein the actuation element is a first actuation element, and wherein the flow control assembly further includes a second actuation element, wherein the second actuation element is composed of a shape memory material and is configured to transition the gating element from the second position to and/or toward the first position.

33. The adjustable flow shunt of claim 31 wherein the flow control assembly further includes an anchoring element designed to conform to a portion of the interior chamber to thereby secure the flow control assembly within the interior chamber.

34. The adjustable flow shunt of claim 33 wherein the actuation element, the gating element, and the anchoring element form a unitary structure formed from a single sheet of material.

35. The adjustable flow shunt of claim 31 wherein the lumen has a rectangular cross-sectional shape.

36. The adjustable flow shunt of claim 31 wherein the frame has a longitudinal cross-sectional dimension of less than about 100 µm.

37. The adjustable flow shunt of claim 31 wherein the frame has a longitudinal cross-sectional dimension of less than about 80 µm.

38. The adjustable flow shunt of claim 31 wherein the frame has a longitudinal cross-sectional dimension of less than about 60 µm.

39. The adjustable flow shunt of claim 31 wherein the bladder portion includes a first longitudinal axis extending therethrough and the elongated portion includes a second longitudinal axis extending therethrough, and wherein the first longitudinal axis is not parallel to the second longitudinal axis.

40. The adjustable flow shunt of claim 39 wherein the first longitudinal axis and the second longitudinal axis form an angle between about 90 degrees and about 180 degrees.

41. The adjustable flow shunt of claim 31 wherein the flow control assembly is at least partially composed of nitinol.

42. The adjustable flow shunt of claim 31 wherein the bladder portion includes a plurality of holes.

* * * * *

UNITED STATES PATENT AND TRADEMARK OFFICE
CERTIFICATE OF CORRECTION

| | | |
|---|---|---|
| PATENT NO. | : 11,517,477 B2 | Page 1 of 1 |
| APPLICATION NO. | : 17/765590 | |
| DATED | : December 6, 2022 | |
| INVENTOR(S) | : Richard Lilly et al. | |

It is certified that error appears in the above-identified patent and that said Letters Patent is hereby corrected as shown below:

In the Claims

Column 25, Line 9, Claim 31, delete "blocking" and insert -- block -- therefor.

Signed and Sealed this
Twenty-eighth Day of October, 2025

John A. Squires
*Director of the United States Patent and Trademark Office*